US007220420B2

(12) United States Patent
Chisari et al.

(10) Patent No.: US 7,220,420 B2
(45) Date of Patent: *May 22, 2007

(54) HEPATITIS C VIRUS-DERIVED PEPTIDES CAPABLE OF INDUCING CYTOTOXIC T LYMPHOCYTE RESPONSES

(75) Inventors: Francis V. Chisari, Del Mar, CA (US); Andreas Cerny, Berne (CH)

(73) Assignee: The Scripps Research Institute, La Jolla, CA (US)

( * ) Notice: Subject to any disclaimer, the term of this patent is extended or adjusted under 35 U.S.C. 154(b) by 835 days.

This patent is subject to a terminal disclaimer.

(21) Appl. No.: 08/854,825

(22) Filed: May 12, 1997

(65) Prior Publication Data

US 2002/0115061 A1    Aug. 22, 2002

Related U.S. Application Data

(63) Continuation of application No. 08/214,650, filed on Mar. 17, 1994, now Pat. No. 5,709,995.

(51) Int. Cl.
*A61K 39/29* (2006.01)

(52) U.S. Cl. .................................... 424/228.1

(58) Field of Classification Search .................. 435/5; 530/300, 324–328; 424/189.1, 228.1
See application file for complete search history.

(56) References Cited

U.S. PATENT DOCUMENTS

| 4,565,697 A | 1/1986 | Ohmura et al. ............... 424/89 |
| 4,599,230 A | 7/1986 | Milich et al. ................. 424/89 |
| 4,599,231 A | 7/1986 | Milich et al. ................. 424/89 |
| 4,624,918 A | 11/1986 | Hershberg .................... 435/68 |
| 4,690,915 A | 9/1987 | Rosenberg ..................... 514/2 |
| 4,803,164 A | 2/1989 | Hitzeman et al. ............. 435/68 |
| 4,882,145 A | 11/1989 | Thornton et al. ............. 424/88 |
| 4,977,092 A | 12/1990 | Bitter .......................... 435/320 |
| 5,017,558 A | 5/1991 | Vyas ............................ 514/14 |
| 5,019,386 A | 5/1991 | Machida et al. ............... 424/89 |
| 5,106,726 A | 4/1992 | Wang ............................ 435/5 |
| 5,196,512 A | 3/1993 | Bianchi et al. ............. 530/326 |
| 5,350,671 A | 9/1994 | Houghton et al. ............. 435/5 |
| 5,372,928 A | 12/1994 | Miyamura et al. ............. 435/5 |

FOREIGN PATENT DOCUMENTS

| EP | 0 154 902 | 9/1985 |
| EP | 0 291 586 | 11/1988 |
| EP | 0 388 232 | 4/1990 |
| EP | 0 463 848 A2 | 2/1992 |
| WO | WO93/00365 | 7/1993 |
| WO | WO93/18054 | 9/1993 |
| WO | WO 93/18054 | 9/1993 |
| WO | WO 95/12677 | 11/1993 |
| WO | WO93/25575 | 12/1993 |
| WO | WO 95/27733 | 4/1994 |
| WO | 94/20127 | 10/1994 |
| WO | WO 95/22317 | 8/1995 |
| WO | WO-A-95/22317 | 8/1995 |

OTHER PUBLICATIONS

Smith et al., 1997, "Oncogenic mutations in ras create HLA-A2.1 binding peptides but affect their extracellular antigen processing," Intl. Immunol. 9(8):1085-1093.*
Nayersina et al., 1993, "HLA A2 restricted cytotoxic T lymphocyte responses to multiple hepatitis B surface antigen epitopes during hepatitis B virus infection," J. Immunol. 150(10):4659-4671.*
Bertoletti et al., 1994, "Cytotoxic T lymphocyte response to a wild type hepatitis B virus epitope in patients chronically infected by variant viruses carrying substitutions within the epitope," J. Exp. Med. 180:933-943.*
Johnson et al., 1992, "Identification of overlapping HLA class I-restricted cytotoxic T cell epitopes in a conserved region of the human immunodeficiency virus type 1 envelope glycoprotein: definition of minimum epitopes and analysis of the effects of sequence variation," J. Exp. Med. 175:961-971.*
Del Val et al., 1991, "Efficient processing of an antigenic sequence for presentation by MCH class I molecules depends on its neighboring residues in the protein," Cell 66:1145-1153.*
Rehermann et al., 1996, "Quantitative analysis of the peripheral blood cytotoxic T lymphocyte response in patients with chronic hepatitis C virus infection," J. Clin. Invest. 98(6):1432-1440.*
Lewin, R., 1987, "When does homology mean something else?," Science 237:1570.*
Reeck et al., 1987, "Homology" in proteins and nucleic acids: a terminology muddle and a way out of it, Cell 50:667.*
Hahn et al., 1992, "CD8+T cell recognition of an endogenously processed epitope is regulated primarily by residues within the epitope," J. Exp. Med. 176:1335-1341.*
Hansen et al., 1993, "The Major Histocompatibility Complex," in *Fundamental Immunology*, Paul, ed., Raven Press, New York, NY, pp. 577-628.*
Koziel et al., 1993, "Hepatitis C virus (HCV)-specific cytotoxic T lymphocytes recognize epitopes in the core and envelope proteins of HCV," J. Virol. 67(12):7522-7532.*

(Continued)

*Primary Examiner*—J. S. Parkin
(74) *Attorney, Agent, or Firm*—Woodcock Washburn LLP

(57) ABSTRACT

The present invention is directed to a molecule comprising a polypeptide having substantial homology with a CTL epitope selected from the group consisting of ADLMGYI-PLV (Core$_{131\text{-}140}$; SEQ ID NO:1), LLALLSCLTV (Core$_{178\text{-}187}$; SEQ ID NO:2), QLRRHIDLLV (SEQ ID NO:55), LLCPAGHAV (NS3$_{1169\text{-}1177}$; SEQ ID NO:26), KLVALGINAV (NS3$_{1406\text{-}1415}$; SEQ ID NO:28), SLMAFTAAV (NS4$_{1789\text{-}1797}$; SEQ ID NO:34), LLFNILGGWV (NS4$_{1807\text{-}1816}$; SEQ ID NO:35), and ILDSFDPLV (NS5$_{2252\text{-}2260}$; SEQ ID NO:42). Such molecules are used for the treatment and prevention of acute or chronic HCV hepatitis; suitable pharmaceutical compositions and methods using such compositions are disclosed.

31 Claims, 4 Drawing Sheets

OTHER PUBLICATIONS

Figure 1:
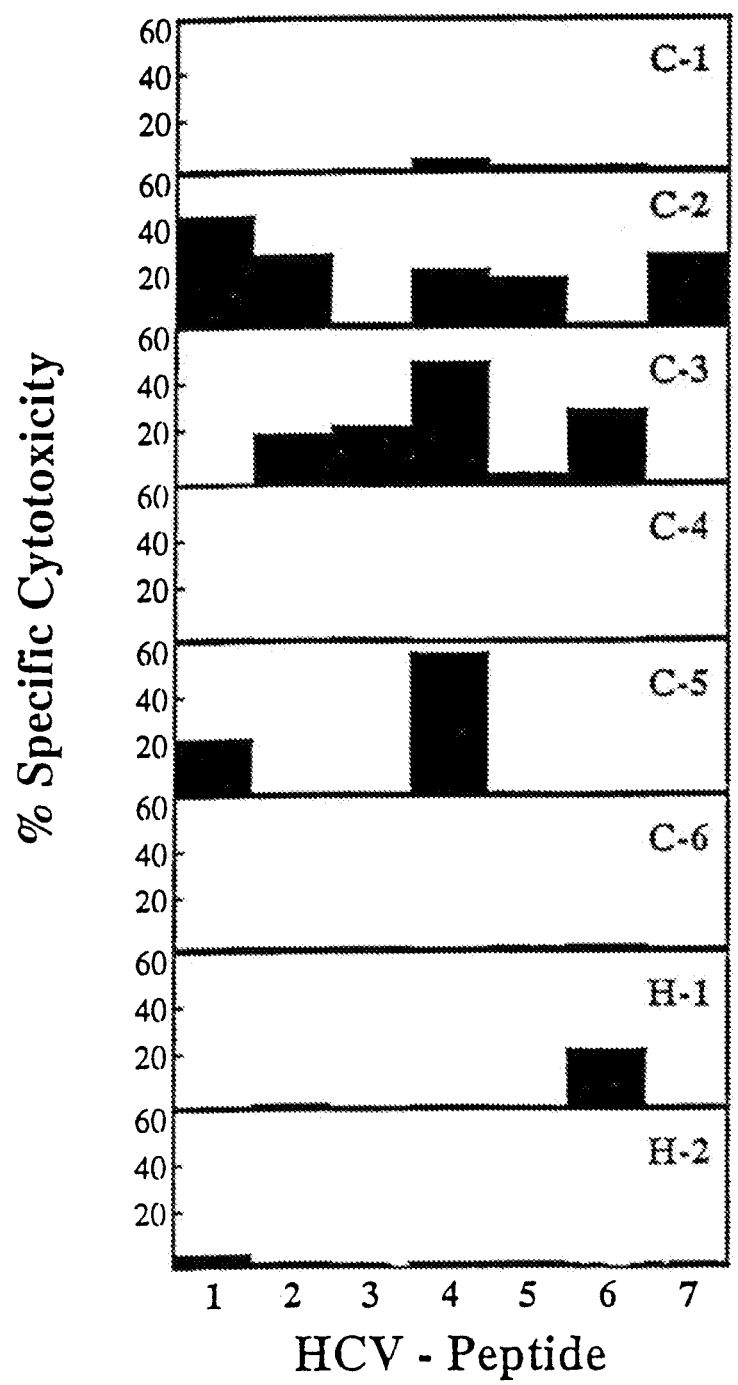

Monaco, J., 1992, "A molecular model of MHC class-I-restricted antigen processing," Immunol. Today 13(5):173-179.*

Koziel et al., 1997, "Characteristics of the intrahepatic cytotoxic T lymphocyte response in chronic hepatitis C virus infection," Springer Semin. Immunopathol. 19:69-83.*

Koff, R., 1993, "A redoubtable obstacle to a hepatitis C vaccine," Gastroenterol. 104(4):1228-1229.*

Prince, A., 1994, "Challenges for development of hepatitis C virus vaccines," FEMS Microbiol. Rev. 14:273-278.*

Boswell et al., 1988, "Sequence comparison and alignment: the measurement and interpretation of sequence similarity," in *Computational Molecular Biology: Sources and Methods for Sequence Analysis*, Lesk, A., ed., Oxford University Press, New York, pp. 161-178.*

Aichele et al., "Antiviral Cytotoxic T Cell Response Induced by In Vivo Priming with a Free Synthetic Peptide," *J. Exp. Med*, 171, 1815-1820 (1990).

Allen et al., "Identification of the T-cell and Ia contact residues of a T-cell antigenic epitope," *Nature* 327, 713-715 (1987).

Alter, "Epidemiology of Community-acquired Hepatitis C," *Viral Hepatitis and Liver Disease*, pp. 410-413 (Hollinger et al., eds. (1991)).

Bukh et al., "Importance of primer selection for the detection of hepatitis C virus RNA with the polymerase chain reaction assay," *Proc. Natl. Acad. Sci. USA*, 89, 187-191 (1992).

Carbone et al., "Induction of Cytotoxic T Lymphocytes by Primary In Vivo Stimulation with Peptides," *J. Exp. Med.*, 167, 1767-1779 (1988).

Cheng et al., "Hepatitis B Virus Large Surface Protein Is Not Secreted but Is Immunogenic when Selectively Expressed by Recombinant Vaccinia Virus," *J. Virol.*, 60, 334-337 (1986).

Choo et al., "Isolation of a cDNA Clone Derived from a Blood-Borne Non-A, Non-B Viral Hepatitis Genome," *Science*, 244, 334-337 (1989).

Choo et al., "Genetic organization and diversity of the hepatitis C virus," *Proc. Natl. Acad. Sci. USA*, 88, 2451-2455 (1991).

Clerici et al., "Detection of Cytotoxic T Lymphocytes Specific for Synthetic Peptides of gp 160 in HIV-Seropositive Individuals," *J. Imm.*, 146, 2214-2219 (1991).

Deres et al., "In vivo priming of virus-specific cytotoxic T lymphocytes with synthetic lipopeptide vaccine," *Nature*, 342, 561-564 (1989).

Dienstag, "Non-A, Non-B Hepatitis. I. Recognition, Epidemiology, and Clinical Features," *Gastroenterology*, 85, 439-462 (1983).

Falk et al., "Allele-specific motifs revealed by sequencing of self-peptides eluted from MHC molecules," *Nature*, 351, 290-296 (1991).

Guo et al., "Different length peptides bind to HLA-Aw68 similarly at their ends but bulge out in the middle," *Nature*, 360, 364-366 (1992).

Harty et al., "CD8 + T Cells Specific for a Single Nonamer Epitope of *Listeria Monocytogenes* Are Protective In Vivo," *J. Exp. Med.*, 175, 1531-1538 (1992).

Houghton et al., "Molecular Biology of the Hepatitis C Viruses: Implications for Diagnosis, Development and Control of Viral Disease," *Hepatology*, 14, 381-388 (1991).

Jansen et al., "Immunotoxins: Hybrid Molecules Combining High Specificity and Potent Cytotoxicity," *Immun. Rev.*, 62, 185-216 (1982).

Jardetzky et al., Identification of self peptides bound to purified HLA-B27, *Nature*, 353, 326-329 (1991).

Kast et al., "Protection against lethal Sendai virus infection by in vivo priming of virus-specific cytotoxic T lymphocytes with a free synthetic peptide," *Proc. Natl. Acad. Sci. USA*, 88, 2283-2287 (1991).

Koziel et al., "Intrahepatic Cytotoxic T Lymphocytes Specific for Hepatitis C Virus in Persons with Chronic Hepatitis," *J. Immunol.*, 149, 3339-3344 (1992).

Lenzi et al., "Antibodies to hepatitis C virus in autoimmune liver disease: evidence for geographical heterogeneity," *Lancet*, 338, 277-280 (1991).

Maryanski et al., "Competitor Analogs for Defined T Cell Antigens: Peptides Incorporating a Putative Binding Motif and Polyproline or Polyglycine Spacers," *Cell*, 60, 63-72 (1990).

Monaco, "A molecular model of MHC class-I-restricted antigen processing," *Immunol. Today*, 13, 173-179 (1992).

Mondelli et al., "Does the Immune Response Play a Role in the Pathogenesis of Chronic Liver Disease?", *Arch. Pathol. Lab. Med.*, 112, 489-497 (1988).

Okamoto et al., "Typing hepatitis C virus by polymerase chain reaction with type-specific primers: application to clinical surveys and tracing infectious sources," *J. Gen. Virol.*, 73, 673-679 (1992).

Roitt et al., *Immunology*, 3d ed., 15.3-15.4 (1993).

Rothbard et al., "Interactions Between Immunogenic Peptides and MHC Proteins," *Ann. Rev. Immunol.*, 9, 527-565 (1991).

Rötzschke et al., "Isolation and analysis of naturally processed viral peptides as recognized by cytotoxic T cells," *Nature*, 348, 252-254 (1990).

Rötzschke et al., "Naturally-occurring peptide antigens derived from the MHC class-I-restricted processing pathway," *Immunol. Today*, 12, 447-455 (1991).

Schumacher et al., "Peptide selection by MHC class I molecules," *Nature*, 350, 703-706 (1991).

Sette et al., "Structural characteristics of an antigen required for its interaction with Ia and recognition by T cells," *Nature*, 328, 395-399 (1987).

Takahasi et al., "Structural Requirements for Class I MHC Molecule-Mediated Antigen Presentation and Cytotoxic T Cell Recognition of an Immunodominant Determinant of the Human Immunodeficiency Virus Envelope Protein," *J. Exp. Med.*, 170, 2023-2035 (1989).

Van Bleek et al., "Isolation of an endogenously processed immunodominant viral peptide from the class I H-2K$^b$ molecule," *Nature*, 348, 213-216 (1990).

Cerny et al., "Cytotoxic T Lymphocytes Restricted by HLA-A2 Specific for Hepatitis C Virus (HCV) Derived Peptides Are Present In The Peripheral Blood Of Patients With Chronic Hepatitis C," *J. Cell. Biochem., Supp. 17D*, 64 (1993).

Cerny et al., "Cytotoxic T Lymphocyte Response to Hepatitis C Virus-derived Peptides Containing the HLA A2.1 Binding Motif," *J. Clin. Invest.*, 95, 521-530 (1995).

Ching et al., "Interaction of immune sera with synthetic peptides corresponding to the structural protein region of hepatitis C virus," *Proc. Natl. Acad. Sci. USA*, 89, 3190-3194 (1992).

Kawahara et al., "Synthetic peptide antigens for detection of hepatitis C virus (HCV) antibody, its composition, and method for using it," *Amino Acids, Peptides, Proteins*, 117, 1013 (1992).

Kita et al., "HLA B44-restricted cytotoxic T lymphocytes recognizing an epitope on hepatitis C virus nucleocapsid protein," *Immunochem.*, 120, 657 (1994).

Hahn et al., 1992, "CD8+ T cell recognition of an endogenously processed epitope is regulated primarily by residues within the epitope," *J. Exp. Med.* 176: 1335-1341.

Eisenlohr et al., 1992, "Flanking sequences influence the presentation of an endogenously synthesized peptide to cytotoxic T lymphocytes," *J. Exp. Med.* 175:481-487.

Hansen et al., 1993, "The major histocompatibility complex, in Fundamental Immunology," Paul, ed., *Raven Press*, New York, NY pp. 577-628.

Koziel et al., 1993 "Hepatitis C virus (HCV)-specific cytotoxic T lymphocytes recognize epitopes in the core and envelope proteins of HCV," *J. Virol.*, 67(12):7522-7532.

Kita et al., 1993, "HLA-B44 restricted cytotoxic T lymphocytes recognizing an epitope on hepatitis C virus nucleocapsid protein," *Hepatol.* 18(5):1039-1044.

Reece et al., 1993, "Mapping the major human T helper epitopes of tetanus toxin," *J. Immunol.* 151:6175-6184.

Shirai et al., 1992 "Broad recognition of cytotoxic T cell epitopes from the HIV-1 envelope protein with multiple class I histocompatibility molecules," *J. Immunol.* 148:1657-1667.

Botarelli et al., 1993, "T-lymphocyte response to hepatitis C virus in different clinical courses of infection," *Gastroenterol.* 104:580-587.

Koff, R., 1993, *Gastroenterol.* 104:1228-1229.

Prince, A., 1994, FEMS *Microbiol. Rev. 14*:273-278.

Penna et al., 1991, "Cytotoxic T Lymphocytes Recognize an HLA-A2-restricted Epitope within the Hepatitis B Virus Nucleocapsid Antigen," *J. Exp. Med. 174*:1565-1570.

Lopez de Castro, 1989, "HLA-B27 and HLA-A2 subtypes: structure, evolution and function," *Immunol. Today*, 10:239-246.

Bertoletti et al., 1991, "HLA class I-restricted human cytotoxic T cells recognize endogenously synthesized hepatitis B virus nucleocapsid antigen," *Proc. Natl. Acad. Sci, USA 88*:10445-10449.

Shirai et al., 1994, "An Epitope in Hepatitis C Virus Core Region Recognized by Cytotoxic T Cells in Mice and Humans," *J. Virol.*, 68:3334-3342.

Battegay, et al., 1995, "Patients with Chronic Hepatitis C Have Circulating Cytotoxic T Cells Which Recognize Hepatitis C Virus-Encoded Peptides Binding to HLA-A2.1 Molecules," *J. Virol. 69*:2462-2470.

Koziel et al., 1995, "HLA Class I-restricted Cytotoxic T Lymphocytes Specific for Hepatitis C Virus," *J. Clin. Invest. 96*:2311-2321.

Lin et al. (1993) "The hepatitis C virus genome: a guide to its conserved sequences and candidate epitopes." Virus Research 30: 27-41.

Falk and Roetzschke, (1993) "Consensus motifs and peptide ligands of MHC class I molecules", seminars in Immunology, 5:81-94.

Cerny A. et al. (1993) Abstract 361 "Cytotoxic T lymphocytes restricted by HLA-A2 specific for HCV derived peptides are present in the peripheral blood of patients with chronic hepatitis C". In Viral hepatitis and Liver Disease pp. 190-194; Proceedings of the International Symposium on Viral hepatitis and Liver Disease: Molecules Today, More Cures Tomorrow; Tokyo, May 10-14, 1993; Eds. Nishioka, K, Suzuke, H., Mishiro, S. and Oda, T. Springer Verlag.

Cerny A., et al. (1994) "HCV-specific cytotoxic T lymphocytes restricted by HLA-A2 are present in the peripheral blood of patients with chronic hepatitis C". Viral Hepatitis and Liver Disease pp. 190-194; Proceedings of the International Symposium on Viral hepatitis and Liver Disease: Molecules Today, More Cures Tomorrow; Tokyo, May 10-14, 1993: Eds. Nishioka, K., Suzuki, H., Mishiro, S. and Oda, T. Springer Verlag.

Farci et al. (1997) "The quasispecies of HCV and the host immune response". Springer Semin Immunopathol. 19: 5-26.

Falk, et al., Seminars in Immunology, vol. 5, pp. 81-94; 1993.

Cerny, et al., "Cytotoxic T lumphocytes restricted by HLA-A2 specific for hepatitis . . . " 1993 Int'l Symposium on Viral Hepatitis and Liver Disease, Tokyo, Japan, May 11-15, 1993.

Cerny, et al., "Hepatitis C Virus specific cytotoxic T lymphocytes . . . " Viral Hepatitis and Liver Disease, pp. 190-194, 1994.

* cited by examiner

SEQUENCE LISTING (1) GENERAL INFORMATION:

(iii) NUMBER OF SEQUENCES: 55

(2) INFORMATION FOR SEQ ID NO:1:

(i) SEQUENCE CHARACTERISTICS:
          (A) LENGTH: 10 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO:1:

Ala Asp Leu Met Gly Tyr Ile Pro Leu Val
1               5                   10

(2) INFORMATION FOR SEQ ID NO:2:

(i) SEQUENCE CHARACTERISTICS:
          (A) LENGTH: 10 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO:2:

Leu Leu Ala Leu Leu Ser Cys Leu Thr Val
1               5                   10

(2) INFORMATION FOR SEQ ID NO:3:

(i) SEQUENCE CHARACTERISTICS:
          (A) LENGTH: 10 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO:3:

Gln Leu Arg Arg His Ile Asp Leu Leu Val
1               5                   10

(2) INFORMATION FOR SEQ ID NO:4:

(i) SEQUENCE CHARACTERISTICS:
          (A) LENGTH: 9 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO:4:

Asp Leu Cys Gly Ser Val Phe Leu Val
1               5

(2) INFORMATION FOR SEQ ID NO:5:

(i) SEQUENCE CHARACTERISTICS:
          (A) LENGTH: 10 amino acids
          (B) TYPE: amino acid
          (C) STRANDEDNESS: single
          (D) TOPOLOGY: unknown (ii) MOLECULE TYPE: peptide (xi) SEQUENCE DESCRIPTION: SEQ ID NO:5:

Leu Leu Ala Pro Gly Ala Lys Gln Asn Val
1               5                   10

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:6:

Leu Leu Leu Thr Thr Thr Gln Trp Gln Val
1               5                   10

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:7:

Leu Leu Thr Thr Thr Gln Trp Gln Val
1               5

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:8:

Gly Leu Ile His Leu His Gln Asn Ile Val
1               5                   10

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:9:

His Leu His Gln Asn Ile Val Asp Val
1               5

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: single

```
        (D) TOPOLOGY: unknown (ii) MOLECULE TYPE: peptide (xi) SEQUENCE DESCRIPTION: SEQ ID NO:10:

Phe Leu Leu Leu Ala Asp Ala Arg Tyr
1               5

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:11:

Ser Leu Ala Gly Thr His Gly Leu Val
1               5

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:12:

Trp Leu Gln Tyr Phe Leu Thr Arg Val
1               5

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:13:

Ile Leu Gln Ser Leu Leu Lys Val
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:14:

Ser Leu Leu Lys Val Pro Val Phe Val
1               5

(2) INFORMATION FOR SEQ ID NO:15:

(i) SEQUENCE CHARACTERISTICS:
        (A) LENGTH: 10 amino acids
        (B) TYPE: amino acid
```

```
            (C) STRANDEDNESS: single
            (D) TOPOLOGY: unknown (ii) MOLECULE TYPE: peptide (xi) SEQUENCE DESCRIPTION: SEQ ID NO:15:

Leu Leu Lys Val Pro Tyr Phe Val Arg Val
 1               5                  10

(2) INFORMATION FOR SEQ ID NO:16:

(i) SEQUENCE CHARACTERISTICS:
            (A) LENGTH: 10 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:16:

Lys Leu Gly Ala Leu Thr Gly Thr Tyr Val
 1               5                  10

(2) INFORMATION FOR SEQ ID NO:17:

(i) SEQUENCE CHARACTERISTICS:
            (A) LENGTH: 9 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:17:

Gly Leu Arg Asp Leu Ala Val Ala Val
 1               5

(2) INFORMATION FOR SEQ ID NO:18:

(i) SEQUENCE CHARACTERISTICS:
            (A) LENGTH: 9 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:18:

Asp Leu Ala Val Ala Val Glu Pro Val
 1               5

(2) INFORMATION FOR SEQ ID NO:19:

(i) SEQUENCE CHARACTERISTICS:
            (A) LENGTH: 10 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:19:

Asp Leu Ala Val Ala Val Glu Pro Val Val
 1               5                  10

(2) INFORMATION FOR SEQ ID NO:20:

(i) SEQUENCE CHARACTERISTICS:
            (A) LENGTH: 9 amino acids
```

```
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:20:

Phe Leu Ala Thr Cys Ile Asn Gly Val
1               5

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:21:

Ile Leu Leu Gly Pro Ala Asp Gly Met Val
1               5                   10

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:22:

Leu Leu Gly Pro Ala Asp Gly Met Val
1               5

(2) INFORMATION FOR SEQ ID NO:23:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:23:

Ser Leu Thr Gly Arg Asp Lys Asn Gln Val
1               5                   10

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:24:

Tyr Leu Val Thr Arg His Ala Asp Val
1               5

(2) INFORMATION FOR SEQ ID NO:25:

(i) SEQUENCE CHARACTERISTICS:
```

(A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:25:

Pro Leu Leu Cys Pro Ala Gly His Ala Val
1               5                   10

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:26:

Leu Leu Cys Pro Ala Gly His Ala Val
1               5

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:27:

Asn Leu Glu Thr Thr Met Arg Ser Pro Val
1               5                   10

(2) INFORMATION FOR SEQ ID NO:28:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:28:

Lys Leu Val Ala Leu Gly Ile Asn Ala Val
1               5                   10

(2) INFORMATION FOR SEQ ID NO:29:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:29:

Glu Leu Thr Pro Ala Glu Thr Thr Val
1               5

(2) INFORMATION FOR SEQ ID NO:30:

```
        (i) SEQUENCE CHARACTERISTICS:
            (A) LENGTH: 9 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:30:

Val Leu Val Ala Tyr Gln Ala Thr Val
1               5

(2) INFORMATION FOR SEQ ID NO:31:

(i) SEQUENCE CHARACTERISTICS:
            (A) LENGTH: 9 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:31:

Pro Leu Leu Tyr Arg Leu Gly Ala Val
1               5

(2) INFORMATION FOR SEQ ID NO:32:

(i) SEQUENCE CHARACTERISTICS:
            (A) LENGTH: 10 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:32:

Asp Leu Glu Val Val Thr Ser Thr Trp Val
1               5                   10

(2) INFORMATION FOR SEQ ID NO:33:

(i) SEQUENCE CHARACTERISTICS:
            (A) LENGTH: 10 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:33:

Cys Leu Ser Thr Gly Cys Val Val Ile Val
1               5                   10

(2) INFORMATION FOR SEQ ID NO:34:

(i) SEQUENCE CHARACTERISTICS:
            (A) LENGTH: 9 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:34:

Ser Leu Met Ala Phe Thr Ala Ala Val
1               5

(2) INFORMATION FOR SEQ ID NO:35:
```

```
        (i) SEQUENCE CHARACTERISTICS:
            (A) LENGTH: 10 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:35:

Leu Leu Phe Asn Ile Leu Gly Gly Trp Val
1               5                   10

(2) INFORMATION FOR SEQ ID NO:36:

(i) SEQUENCE CHARACTERISTICS:
            (A) LENGTH: 10 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:36:

Gly Leu Ala Gly Ala Ala Ile Gly Ser Val
1               5                   10

(2) INFORMATION FOR SEQ ID NO:37:

(i) SEQUENCE CHARACTERISTICS:
            (A) LENGTH: 9 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:37:

Ile Leu Ala Gly Tyr Gly Ala Gly Val
1               5

(2) INFORMATION FOR SEQ ID NO:38:

(i) SEQUENCE CHARACTERISTICS:
            (A) LENGTH: 9 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:38:

Ile Leu Ser Pro Gly Ala Leu Val Val
1               5

(2) INFORMATION FOR SEQ ID NO:39:

(i) SEQUENCE CHARACTERISTICS:
            (A) LENGTH: 10 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:39:

Leu Leu Arg Glu Glu Val Ser Phe Arg Val
1               5                   10
```

(2) INFORMATION FOR SEQ ID NO:40:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:40:

```
Gln Leu Pro Cys Glu Pro Glu Pro Asp Val
1               5                   10
```

(2) INFORMATION FOR SEQ ID NO:41:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:41:

```
Arg Leu Ala Arg Gly Ser Pro Pro Ser Val
1               5                   10
```

(2) INFORMATION FOR SEQ ID NO:42:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:42:

```
Ile Leu Asp Ser Phe Asp Pro Leu Val
1               5
```

(2) INFORMATION FOR SEQ ID NO:43:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:43:

```
Pro Leu Pro Pro Lys Ser Pro Pro Val
1               5
```

(2) INFORMATION FOR SEQ ID NO:44:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:44:

```
Asp Leu Ser Asp Gly Ser Trp Ser Thr Val
1               5                   10
```

(2) INFORMATION FOR SEQ ID NO:45:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:45:

Ser Leu Leu Arg His His Asn Leu Val
1           5

(2) INFORMATION FOR SEQ ID NO:46:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:46:

Val Leu Asp Ser His Tyr Gln Asp Val
1           5

(2) INFORMATION FOR SEQ ID NO:47:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:47:

Arg Leu Ile Val Phe Pro Asp Leu Gly Val
1           5               10

(2) INFORMATION FOR SEQ ID NO:48:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:48:

Gly Leu Gln Asp Cys Thr Met Leu Val
1           5

(2) INFORMATION FOR SEQ ID NO:49:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:49:

Met Leu Val Cys Gly Asp Asp Leu Val
1           5

(2) INFORMATION FOR SEQ ID NO:50:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:50:

```
Met Leu Val Cys Gly Asp Asp Leu Val Val
1               5                   10
```

(2) INFORMATION FOR SEQ ID NO:51:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:51:

```
Glu Leu Ile Thr Ser Cys Ser Ser Asn Val
1               5                   10
```

(2) INFORMATION FOR SEQ ID NO:52:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:52:

```
Ile Leu Met Thr His Phe Phe Ser Val
1               5
```

(2) INFORMATION FOR SEQ ID NO:53:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:53:

```
Cys Leu Leu Leu Leu Ala Ala Gly Val
1               5
```

(2) INFORMATION FOR SEQ ID NO:54:

(i) SEQUENCE CHARACTERISTICS:
        (A) LENGTH: 9 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:54:

```
Asp Leu Met Gly Tyr Ile Pro Leu Val
```

```
(2) INFORMATION FOR SEQ ID NO:55:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:55:

Gln Leu Arg Arg His Ile Asp Leu Leu Val
1               5                   10
```

HEPATITIS C VIRUS-DERIVED PEPTIDES CAPABLE OF INDUCING CYTOTOXIC T LYMPHOCYTE RESPONSES

This is a continuation of U.S. application Ser. No. 08/214,650, filed Mar. 17, 1994, now U.S. Pat. No. 5,709,995.

GOVERNMENT SUPPORT

The U.S. Government may have certain rights in this invention pursuant to Grant No. AI20001 awarded by the National Institutes of Health.

TECHNICAL FIELD OF THE INVENTION

The present invention relates to the isolation and use of compounds having substantial homology to hepatitis C virus-specific cytotoxic T cell lymphocyte epitopes for the immunization and treatment of mammals afflicted with or at risk of exposure to chronic and acute hepatitis C viral hepatitis.

BACKGROUND OF THE INVENTION

Hepatitis C virus ("HCV") was originally identified as a causative agent of transfusion-associated hepatitis that had a propensity to induce acute and chronic hepatitis and hepatocellular carcinoma. Choo et al., *Science*, 244, 359–362 (1989). It is a major cause of morbidity and mortality worldwide, considering that at least 50% of infected persons will develop chronic hepatitis, and 20% of these will further develop cirrhosis. Dienstag, *Gastroenterology*, 85, 439 (1983). No cure is currently available for treatment of chronic or acute HCV infection.

The complete nucleotide sequence and genetic organization of HCV has been fully elucidated by Choo et al., *Proc. Natl. Acad. Sci. USA*, 88, 2451–2455 (1991). The HCV genome of positive-stranded RNA consists of 9,379 nucleotides and has a single large open reading frame that could encode a viral polyprotein precursor of 3,011 amino acids. Although there is little overall similarity in sequence between that of HCV and other viruses whose sequence is known, a portion of the sequence (upstream of the 5' end of the open reading frame) is similar to the analogously positioned sequence of pestiviral genomes. The polyprotein also displays significant sequence similarity to helicases encoded by animal pestiviruses and human flaviviruses, among others. Comparison of the hydrophobicity profiles of the sequence of encoded amino acids, and comparison of such a profile between HCV and a flavivirus (yellow fever virus), for example, has resulted in the assignment of regions of the HCV genome as relating to proteins forming the capsid or core (C), and the envelope (E1 and E2), as well as five regions that specify nonstructural proteins (NS1 through NS5).

The mechanisms whereby HCV causes acute hepatocellular injury and initiates the sequence of events leading to chronic liver disease and ultimately to hepatocellular carcinoma are not well understood. It is possible that both virus-related direct and immunologically-mediated indirect mechanisms play important roles in HCV chronic hepatitis. For example, a link between HCV infection and the presence of autoantibodies is well-established. Lenzi et al., *Lancet*, 338, 277–280 (1991). Unfortunately, analysis of the direct cytopathic effect of HCV for host liver cells has been hampered due to the lack of suitable animal models and tissue culture systems.

Several clinical observations support the hypothesis that the host immune response contributes to liver cell injury: first, infection acquired early in life occurring in an immunologically immature host leads to a chronic asymptomatic carrier state; second, chronic carriers without evidence of liver cell injury are common; and third, immunosuppression has a beneficial effect on liver cell injury in chronic hepatitis C. See Alter, in *Viral Hepatitis And Liver Disease*, (Hollinger et al., eds., 1991), 410–413. A recent report also demonstrated the presence of an HCV-specific, major histocompatibility complex ("HLA" or "MHC") class I-restricted cytotoxic T cell ("CTL") response in liver-infiltrating lymphocytes from two patients afflicted with chronic HCV hepatitis. Koziel et al., *J. Immunol.*, 149, 3339–3344 (1992). More specifically, it is generally presumed that the > response to viral antigens is almost entirely T-cell dependent. Even the antibody response requires T-cell help. Thus susceptibility to virus infections is particularly associated with T cell dysfunction, though this tells us little about the effector mechanisms involved, since T cells are required both for antibody production and for some cytotoxic reactions.

Roitt et al., *Immunology* (3d ed. 1993) at 15.3.

Accordingly, central to the host immune response to attack by an intracellular agent (e.g., an infecting virus, bacterium, or other intracellular parasite) would be that which is mediated by the cellular immune system; in particular, by HLA class I CTL's. Class I antigens are cell surface glycoproteins that control the recognition by CTL's of modified (i.e., infected or otherwise altered, as in cancer) self cells, and of foreign cells. CTL-mediated lysis of virus infected host cells may lead to clearance of the virus or, if incomplete, such lysis may lead to viral persistence and eventually chronic tissue injury. Viral persistence and immunologically-mediated liver injury are thought to be important mechanisms leading to chronic hepatitis C after infection with HCV.

At its most fundamental level, the cellular immune response involves a multimolecular interaction between antigenic peptides, HLA molecules and T cell receptors ("TCR") on the CTL. Unlike antigen recognition by B cell immunoglobulin receptors, the two general classes of T cells do not recognize native antigen in solution; rather, they recognize short antigenic peptides that have reached the cell surface via two quite different pathways (reviewed in Rothbard et al., *Ann. Rev. Immunol.*, 9, 527–565 (1991); also, see Rötzschke et al., *Immunol. Today*, 12, 447–455 (1991)). The subject matter of the present invention centers on the induction of activity by one of these pathways, namely that involving the human CD8$^+$ T cell and its counterpart in other mammalian species.

Human CD8$^+$ T cells recognize short antigenic peptides (usually 9–11 residues in length) once presented to the antigen binding groove of HLA class I molecules. The antigen binding grooves, and, more generally, HLA class I molecules, are present at the surface of the cells in which each HLA class I molecule's precursor proteins were originally synthesized. As reported by Monaco (*Immunol. Today*, 13, 173–179 (1992)), such precursor proteins may be derived from an infecting virus. Accordingly, the antigenic peptides, processed within the CTL, are derived by proteolytic cleavage of endogenously synthesized antigen in the cytoplasm. The processed peptides are then bound by a family of transporter proteins (encoded within the HLA locus) that shuttle them into the lumen of the endoplasmic reticulum where they are scanned for the presence of HLA allele specific binding motifs by the antigen binding domain of resident HLA class I proteins. Peptides containing the appropriate motif are bound by the corresponding HLA class I molecule, which then associates with $\beta_2$-microglobulin and moves to the cell surface as an integral membrane protein. At the cell surface, the integral membrane protein can present the antigenic peptide to the appropriately rearranged TCR on a $CD8^+$ T cell. The T cell subset specificity of this interaction derives from the fact that the multimolecular HLA-peptide-TCR complex is stabilized by accessory interactions such as those between the CD8 molecule on the T cell and the HLA class I molecule involved in the complex.

At the present time, it is difficult to predict from the sequence of an antigenic protein how the protein will be processed and which peptide portions will bind HLA class I molecules and be presented to CTL's. Binding motifs have been predicted for some HLA class I molecules based on sequence analysis of peptides eluted from these molecules. Falk et al., *Nature,* 351, 290 (1991). However, not all peptides that match the motif will be recognized as CTL-recognizable epitopes. Moreover, even of the peptides that are processed and bind to HLA class I molecules, identifying which ones will contain CTL-recognizable epitopes is not yet predictable.

Due to work in other systems, it has been assumed that the HLA class I restricted, $CD8^+$ CTL response to endogenously synthesized HCV antigens is responsible for the observed pathological consequences of chronic infection by this virus. Mondelli et al., *Arch. Pathol. Lab. Med.,* 112, 489 (1988). This hypothesis was untestable until recently due to the absence of the necessary reagents and experimental systems. HCV has not been demonstrated to infect continuous human cell lines in tissue culture, and the only animal model of HCV (chimpanzee) infection that could be used for such studies involves a species for which the immune system is not sufficiently defined.

Irrespective of the mode of activity, it is evident that the CTL response with respect to HCV is deficient in cases of chronic HCV disease. Moreover, there are a large number of individuals who, having been infected with HCV, have since developed chronic HCV hepatitis. It would be desirable to stimulate the immune response in these individuals to respond to appropriate HCV antigens and thereby eliminate their infection. It would also be desirable to prevent the progression of an acute phase HCV infection to a chronic phase infection. Further, as there is no currently available vaccine for HCV infection of any sort, it would be desirable to establish such a vaccine, preferably based on a range of antigenic determinants. Accordingly, it is an object of the present invention to provide agents that strengthen or boost the cellular immune system to fight HCV hepatitis. It is a further object to provide pharmaceutical compositions that strengthen or boost the cellular immune system for fighting HCV hepatitis, both with reference to therapeutic and prophylactic uses.

These and other objects and advantages of the present invention, as well as additional inventive features, will be apparent from the description of the invention provided herein.

BRIEF SUMMARY OF THE INVENTION

The present invention provides agents that strengthen or boost the cellular immune system to fight or prevent HCV hepatitis infection. In particular, the present invention is directed to a polypeptide having substantial homology with a CTL epitope selected from the group consisting of ADLMGYIPLV ($Core_{131-140}$; SEQ ID NO:1), LLALLSCLTV ($Core_{178-187}$; SEQ ID NO:2), LLCPAGHAV ($NS3_{1169-1177}$; SEQ ID NO:26), KLVALGINAV ($NS3_{1406-1415}$; SEQ ID NO:28), SLMAFTAAV ($NS4_{1789-1797}$; SEQ ID NO:34), LLFNILGGWV ($NS4_{1807-1816}$; SEQ ID NO:35), ILDSFDPLV ($NS5_{2252-2260}$; SEQ ID NO:42), DLMGYIPLV ($Core_{132-140}$; SEQ ID NO:54) and QLRRHIDLLV ($E1_{257-266}$; SEQ ID NO:3), or to a molecule that comprises such a polypeptide. In addition, the present invention provides a method of provoking an immune response to a hepatitis C viral antigen, comprising contacting a suitable cytotoxic T lymphocyte with an immune response provoking effective amount of a molecule comprising a peptide selected from the group of epitopes listed above, and further provides pharmaceutical compositions comprising at least one of the CTL-specific epitopes.

BRIEF DESCRIPTION OF THE DRAWINGS

FIG. 1 is a bar graph that displays HCV-specific CTL responses observed after initial in vitro expansion of the CTL's in the presence of HCV-derived peptides. The abscissa sets forth each of seven HCV peptides (detailed in Example 3) and the ordinate sets forth the percentage specific cytotoxicity.

FIG. 2 is a set of three graphs that display cytotoxic activity of CTL lines specific for three HCV peptides (detailed in Example 3). The abscissa sets forth the effector/target cell ratio and the ordinate sets forth the percentage specific lysis.

FIG. 3 is a set of four graphs that displays the results of a HLA class I restriction analysis (detailed in Example 3). The abscissa sets forth the effector/target cell ratio and the ordinate sets forth the percentage specific lysis.

FIG. 4 is a set of two graphs that demonstrates the results of an assay regarding the recognition and lysis of target cells that have been caused to synthesize specific viral antigen endogenously (detailed in Example 3). The abscissa sets forth the effector/target cell ratio and the ordinate sets forth the percentage specific lysis.

DESCRIPTION OF THE PREFERRED EMBODIMENTS

The present invention provides certain polypeptides that stimulate HLA class I restricted cytotoxic T lymphocyte ("CTL") responses against certain HCV antigens, particularly when such antigens are expressed in a host cell that has been infected by HCV. Such polypeptides are useful in compositions and methods for the treatment, prevention, and diagnosis of HCV infection, whether in its acute or chronic phase. The stimulated CTL's kill HCV-infected cells, thereby preventing, impeding, or reversing the course of HCV infection. Novel combinations of epitopes are contemplated within the context of the present invention, such that the CTL response described in brief above, and in greater detail below, is combined with a T-helper response or multiple CTL response directed at different HCV antigens, for example.

The polypeptides of interest are derived from various regions of the HCV genome, including the core (e.g., ADLMGYIPLV ($Core_{131-140}$; SEQ ID NO:1) and LLALLSCLTV ($Core_{178-187}$; SEQ ID NO:2)), NS3 (e.g., LLCPAGHAV ($NS3_{1169-1177}$; SEQ ID NO:26) and KLVALGINAV ($NS3_{1406-1415}$; SEQ ID NO:28)), NS4 (e.g., SLMAFTAAV ($NS4_{1789-1797}$; SEQ ID NO:34) and LLFNILG- GWV (NS4$_{1807-1816}$; SEQ ID NO:35)), NS5 (e.g., ILDSFDPLV (NS5$_{2252-2260}$; SEQ ID NO:42)). Numeric positions on the HCV genome are in accordance with Choo et al., *Proc. Natl. Acad. Sci. USA,* 88, 2451–2455 (1991).

In certain embodiments of the present invention, the polypeptides of interest will have the sequences just recited as well as others listed below, or will have sequences that are substantially homologous thereto. Two polypeptides are said to be substantially homologous if at least 50% of the amino acid ("aa") residues are the same in the same or analogous position. By analogous position, it is intended the relative position of the polypeptide of interest itself, regardless of any flanking polypeptide or other chemical elements that may be attached to the polypeptide of interest.

Preferred peptides employed in the subject invention, accordingly, need not be identical, but are at least substantially homologous, to the following peptides: ADLMGYIPLV (Core$_{131-140}$; SEQ ID NO:1), DLMGYIPLV (Core $_{132-140}$; SEQ ID NO:54), LLALLSCLTV (Core$_{178-187}$; SEQ ID NO:2), LLCPAGHAV (NS3$_{1169-1177}$; SEQ ID NO:26), KLVALGINAV (NS3$_{1406-1415}$; SEQ ID NO:28), SLMAFTAAV (NS4$_{1789-1797}$; SEQ ID NO:34), LLFNILGGWV (NS4$_{1807-1816}$; SEQ ID NO:35), ILDSFDPLV (NS5$_{2252-2260}$; SEQ ID NO:42), and QLRRHIDLLV (E1$_{257-266}$; SEQ ID NO:3). The subject compounds have the ability to stimulate cytotoxic T lymphocytic activity against at least one major subtype of HCV. Such subtypes of HCV have been described by Houghten et al., *Hepatology,* 14, 381–388 (1991).

The present invention relates to a polypeptide having substantial homology with a CTL epitope selected from the same group of polypeptides identified above. Preferred polypeptides include LLCPAGHAV (NS3$_{1169-1177}$; SEQ ID NO:26), KLVALGINAV (NS3$_{1406-1415}$; SEQ ID NO:28), SLMAFTAAV (NS4$_{1789-1797}$; SEQ ID NO:34), LLFNILGGWV (NS4$_{1807-1816}$; SEQ ID NO:35), ILDSFDPLV (NS5$_{2252-2260}$; SEQ ID NO:42), and those substantially homologous thereto. More preferred polypeptides include LLCPAGHAV (NS3$_{1169-1177}$; SEQ ID NO:26), KLVALGINAV (NS3$_{1406-1415}$; SEQ ID NO:28), and those substantially homologous thereto. The most preferred polypeptides are KLVALGINAV (NS3$_{1406-1415}$; SEQ ID NO:28), and those substantially homologous thereto.

In particular, the present invention relates to a suitable molecule comprising a polypeptide having substantial homology with one of the CTL epitopes recited above. The molecule of the present invention comprises at least five amino acids and as many as 50 amino acids. A preferred range of amino acids for the molecule of the present invention is from about eight amino acids to less than about twenty-five amino acids or to less than about 50 amino acids. A more preferred range of amino acids is from about nine amino acids to less than about fifteen. A most preferred range of amino acids is from about nine amino acids to less than about 13 amino acids.

It may be desirable to optimize peptides of the invention to a length of eight to twelve amino acid residues, commensurate in size with endogenously processed viral peptides that are bound to major histocompatibility complex ("MHC") class I molecules on the cell surface. See generally, Schumacher et al., *Nature,* 350, 703–706 (1991); Van Bleek et al., *Nature,* 348 213–216 (1990); Rotzschke et al., *Nature,* 348, 252–254 (1990); and Falk et al., *Nature,* 351, 290–296 (1991). As set forth in more detail below, usually the peptides will have at least a majority of amino acids that are homologous to a corresponding portion of contiguous residues of the HCV sequences disclosed hereinabove, and contain a CTL-inducing epitope.

The peptides of the present invention can be prepared by any suitable means, such as synthetically using standard peptide synthesis chemistry (described hereinbelow) or by using recombinant DNA technology (also described below). Although the peptide preferably will be substantially free of other naturally occurring HCV proteins and fragments thereof, in some embodiments the peptides can be synthetically conjugated to native fragments or particles, or other compounds that are nonproteinaceous. The term peptide is used interchangeably with polypeptide or oligopeptide in the present specification to designate a series of amino acids connected one to the other by peptide bonds between the alpha-amino and alpha-carboxy groups of adjacent amino acids. The polypeptides or peptides can be any suitable length, either in their neutral (actually zwitterionic) forms or in forms that are salts, and either free of modifications, such as glycosylation, side chain oxidation, or phosphorylation, or containing these modifications, subject to the condition that the modification not destroy the biological activity of the polypeptides, as herein described.

Desirably, the peptide will be as small as possible while still maintaining substantially all of the biological activity of the larger peptides first disclosed herein. By biological activity is meant the ability to bind an appropriate MHC molecule and induce a cytotoxic T lymphocyte response against HCV antigen or antigen mimetic. By a cytotoxic T lymphocyte response is meant a CD8$^+$ T lymphocyte response specific for an HCV antigen of interest, wherein CD8$^+$, MHC class I-restricted T lymphocytes are activated. The activated T lymphocytes secrete lymphokines (e.g., gamma interferon) and liberate other products (e.g., serine esterases) that inhibit viral replication in infected autologous cells or transfected cells, with or without cell killing.

Various modifications can be effected at noncritical amino acid positions within the polypeptide of interest without substantially disturbing its biological activity. Such modifications include, but are not limited to, substitutions, deletions and additions of other peptidyl residues, $C_1$–$C_7$ alkyl or $C_1$–$C_{10}$ aralkyl, as further discussed below.

A majority of the amino acids of the polypeptides of the present invention will be identical or substantially homologous to the amino acids of the corresponding portions of naturally occurring HCV proteins or epitopes identified above, wherein the selected polypeptide can be flanked and/or modified at one or both termini as described herein.

Accordingly, the molecule of the present invention in one of its embodiments comprises a polypeptide as described hereinabove that has conjugated thereto a substance, wherein the substance is selected from the group consisting of a radiolabel, an enzyme, a fluorescent label, a solid matrix, a carrier, and a second CTL epitope. The substance can be conjugated to the polypeptide at any suitable position, including the N and C termini and points in between, depending on the availability of appropriate reactive groups in the side chains of the constituent amino acids of the polypeptide of interest. Additionally, the substance can be conjugated directly to the polypeptide or indirectly by way of a linker. Preferred radiolabels include $^3$H, $^{14}$C, $^{32}$P, $^{35}$S, $^{125}$I, and other suitable radiolabels for use in various radioimmunoassays and the like. Preferred fluorescent labels include fluorescein, rhodamine, and other suitable fluorescent labels for use in fluorescent assays and the like. Preferred enzymes include alkaline phosphatase and other suitable enzymes useful for any suitable purpose, including as a marker in an assay procedure. Preferred solid matrices are glass, plastic, or other suitable surfaces, including various resins such as Sephadex® chromatography media and the like. Preferred carriers include immunogenic lipids, proteins, and other suitable compounds, such as a liposome or bovine serum albumin. Preferred second CTL epitopes include T-helper specific antigens, antigens that would foster a B cell response, and other suitable antigens that stimulate CTL's.

Additional amino acids can be added to the termini of a peptide of the present invention to provide for ease of linking peptides one to another, for coupling to a carrier, support or a larger peptide, for reasons discussed herein, or for modifying the physical or chemical properties of the peptide, and the like. Suitable amino acids, such as tyrosine, cysteine, lysine, glutamic or aspartic acid, and the like, can be introduced at the C- or N-terminus of the peptide. In addition, the peptide of the present invention can differ from the natural sequence by being modified by terminal-$NH_2$ acylation, e.g., acetylation, or thioglycolic acid amidation, terminal-carboxy amidation, e.g., ammonia, methylamine, etc. In some instances these modifications may provide sites for linking to a support or other molecule, thereby providing a linker function.

It is understood that the HCV peptides of the present invention or analogs or homologs thereof that have cytotoxic T lymphocyte stimulating activity may be modified as necessary to provide certain other desired attributes, e.g., improved pharmacological characteristics, while increasing or at least retaining substantially the biological activity of the unmodified peptide. For instance, the peptides can be modified by extending, decreasing or substituting amino acids in the peptide sequence by, for example, the addition or deletion of suitable amino acids on either the amino terminal or carboxy terminal end, or both, of peptides derived from the sequences disclosed herein.

The peptides may be modified to enhance substantially the CTL inducing activity, such that the modified peptide analogs have CTL activity greater than a peptide of the wild-type sequence. For example, it may be desirable to increase the hydrophobicity of the N-terminal of a peptide, particularly where the second residue of the N-terminal is hydrophobic and is implicated in binding to the HLA restriction molecule. By increasing hydrophobicity at the N-terminal, the efficiency of the presentation to T cells may be increased. Peptides prepared from other disease associated antigens, particularly those containing CTL inducing epitopes for which a host may not have significant CTL activity, may be made CTL-inducing by substituting hydrophobic residues at the N-terminus of the peptide where the second residue is normally hydrophobic.

Therefore, the peptides may be subject to various changes, such as insertions, deletions, and substitutions, either conservative or non-conservative, where such changes provide for certain advantages in their use. By conservative substitutions is meant replacing an amino acid residue with another that is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Preferably, the portion of the sequence that is intended to mimic substantially a HCV cytotoxic T lymphocyte stimulating epitope will not differ by more than about 20% from the sequence of at least one subtype of HCV, except where additional amino acids may be added at either terminus for the purpose of modifying the physical or chemical properties of the peptide for, for example, ease of linking or coupling, and the like. Where regions of the peptide sequences are found to be polymorphic among HCV subtypes, it may be desirable to vary one or more particular amino acids to mimic more effectively differing cytotoxic T-lymphocyte epitopes of different HCV strains or subtypes.

Within the peptide sequences identified by the present invention, including the representative peptides listed above, there are residues (or those that are substantially functionally equivalent) that allow a particular peptide to retain its biological activity, i.e., the ability to stimulate a class I-restricted cytotoxic T-lymphocytic response against HCV-infected cells or cells that express HCV antigen. These residues can be identified by suitable single amino acid substitutions, deletions, or insertions, followed by suitable assays, such as testing for cytotoxic activity by so-stimulated CTL's.

In addition, the contributions made by the side chains of the residues can be probed via a systematic replacement of individual residues with a suitable amino acid, such as Gly or Ala. Systematic methods for determining which residues of a linear amino acid sequence are required for binding to a specific MHC protein, one of the characteristics of the peptides of the present invention, are known. See, for instance, Allen et al., *Nature*, 327, 713–717; Sette et al., *Nature*, 328, 395–399; Takahashi et al., *J. Exp. Med.*, 170, 2023–2035 (1989); and Maryanski et al., *Cell*, 60, 63–72 (1990).

Peptides that tolerate multiple amino acid substitutions generally incorporate small, relatively neutral molecules, e.g., Ala, Gly, Pro, or similar residues. The number and types of residues that can be substituted, added or subtracted will depend on the spacing necessary between the essential epitopic points and certain conformational and functional attributes that are sought. By types of residues, it is intended, e.g., to distinguish between hydrophobic and hydrophilic residues, among other attributes. If desired, increased binding affinity of peptide analogs to its MHC molecule for presentation to a cytotoxic T-lymphocyte can also be achieved by such alterations. Generally, any spacer substitutions, additions or deletions between epitopic and/or conformationally important residues will employ amino acids or moieties chosen to avoid stearic and charge interference that might disrupt binding.

Peptides that tolerate multiple substitutions while retaining the desired biological activity may also be synthesized as D-amino acid-containing peptides. Such peptides may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the antigenic peptide.

In addition to the exemplary peptides described herein, the present invention provides methods for identifying other epitopic regions associated with said peptide regions capable of inducing MHC-restricted cytotoxic T lymphocyte responses against HCV. The methods comprise obtaining peripheral blood lymphocytes (PBL) from infected and uninfected individuals and exposing (i.e., stimulating) the PBL cells with synthetic peptide or polypeptide fragments derived from a peptide region (e.g., core region (e.g., ADLMGYIPLV (Core$_{131-140}$; SEQ ID NO:1) and LLA- LLSCLTV (Core$_{178-187}$; SEQ ID NO:2)), NS3 (e.g., LLCPAGHAV (NS3$_{1169-1177}$; SEQ ID NO:26) and KLVALGINAV (NS3$_{1406-1415}$; SEQ ID NO:28)), NS4 (e.g., SLMAFTAAV (NS4$_{1789-1797}$; SEQ ID NO:34) and LLFNILGGWV (NS4$_{1807-1816}$; SEQ ID NO:35)), and NS5 (e.g., ILDSFDPLV (NS5$_{2252-2260}$; SEQ ID NO:42)). The peptides DLMGYIPLV (Core$_{132-140}$; SEQ ID NO:54) and QLRRHIDLLV (E1$_{257-266}$; SEQ ID NO:3) are useful in this regard as well.

Pools of overlapping synthetic peptides randomly selected from the HCV sequence, each typically about 8 to 20 residues long, preferably 9–12 residues, can be used to stimulate the cells. Alternatively, as exemplified below in Example 1 for HLA-A2 specific CTL epitopes, peptides fitting a binding motif for CTL-directed antigens of a particular HLA class I allele (Falk et al., *Nature*, 351, 290–296 (1991)) were selected for testing. It is contemplated that peptides fitting the analogous binding motifs for other HLA class I alleles, such as HLA-Aw68 (Guo et al., *Nature*, 360, 364–366 (1992)) or HLA-B27 (Jardetzky et al., *Nature*, 353, 326–329 (1991)), among others, may be identified by following the methods disclosed herein, and accordingly are viewed as part of the present invention. Active peptides can be selected from pools that induce cytotoxic T lymphocyte activity. The ability of the peptides to induce specific cytotoxic activity is determined by incubating the stimulated PBL cells with autologous labeled (e.g., $^{51}$Cr) target cells (such as HLA matched macrophages, T cells, fibroblasts or B lymphoblastoid cells) infected or transfected with the HCV subgenomic fragments thereof, such that the targeted antigen is synthesized endogenously by the cell (or the cell is pulsed with the peptide of interest), and measuring specific release of label.

Once a peptide having an epitopic region that stimulates a cytotoxic T lymphocyte response is identified, the MHC restriction element of the response can be determined and/or confirmed. This involves incubating the stimulated PBL or short term lines thereof with a panel of (labeled) target cells or known HLA types that have been pulsed with the peptide of interest, or appropriate controls. The HLA allele(s) of cells in the panel that are lysed by the CTL are compared to cells not lysed, and the HLA restriction element(s) for the cytotoxic T lymphocyte response to the antigen of interest is identified.

Carbone et al., *J. Exp. Med.*, 167, 1767 (1988), have reported that stimulation with peptides may induce cytotoxic T lymphocytes with low affinity for corresponding endogenous protein, such that repetitive peptide stimulation may yield cytotoxic T lymphocytes that recognize peptide but not native antigen. As the inability of stimulated cytotoxic T lymphocytes to recognize native HCV proteins would be undesirable in the development of HCV peptide therapeutics and vaccine compositions, methods to circumvent this potential limitation are used. A sequential restimulation of cytotoxic T cells is employed in the present invention to identify and select T cells with a higher affinity for naturally processed antigen than for a synthetic peptide. Short term cytotoxic T lymphocyte lines are established by restimulating activated PBL. Cells stimulated with peptide are restimulated with peptide and recombinant or native HCV antigen, e.g., NS3 derived peptide. Cells having activity are also stimulated with an appropriate T cell mitogen, e.g., phytohemagglutinin (PHA). The restimulated cells are provided with irradiated allogeneic PBLs as an antigen nonspecific source of T cell help, and HCV antigen. To expand selectively the population of cytotoxic T lymphocytes that recognize native HCV antigen and to establish long term lines, a sample of PBL from a patient is first stimulated with peptide and recombinant or native HCV antigen, followed by restimulation with HLA-matched B lymphoblastoid cells that stably express the corresponding HCV antigen polypeptide. The cell lines are re-confirmed for the ability to recognize endogenously synthesized antigen using autologous and allogeneic B-lymphoblastoid or other cells transfected or infected so as to produce the appropriate antigen.

Having identified different peptides of the invention that contribute to inducing anti-HCV cytotoxic T lymphocyte responses in one or more patients or HLA types, in some instances it may be desirable to join two or more peptides in a composition, either by chemical linkage or as a physical mixture. The peptides in the composition can be identical or different, and together they should provide equivalent or greater biological activity than the parent peptide(s). For example, using the methods described herein, two or more peptides may define different or overlapping cytotoxic T lymphocyte epitopes from a particular region, e.g. NS3 as in LLCPAGHAV (NS3$_{1169-1177}$; SEQ ID NO:26) and KLVALGINAV (NS3$_{1406-1415}$; SEQ ID NO:28), which peptides can be combined in a "cocktail" to provide enhanced immunogenicity for cytotoxic T lymphocyte responses. Moreover, suitable peptides of one region can be combined with suitable peptides of other HCV regions, from the same or different HCV protein, particularly when a second or subsequent peptide has a MHC restriction element different from the first. The present disclosure includes HCV epitope sequences derived from Core, E, NS3, NS4, and NS5 regions.

This composition of peptides can be used effectively to broaden the immunological coverage provided by therapeutic, prophylactic, or diagnostic methods and compositions of the present invention for the benefit of a diverse population. For example, the different frequencies of HLA alleles among prevalent ethnic groups (Caucasian, asian and african blacks) are shown in the following table. Therapeutic or vaccine compositions of the invention may be formulated to provide potential therapy or immunity to as high a percentage of a population as possible.

| HLA ALLELE FREQUENCIES ANONG PREVALENT ETHNIC GROUPS | | | | |
| --- | --- | --- | --- | --- |
| HLA Allele | EUC | NAC | AFR | JPN |
| A2 | 45.3 | 46.6 | 27.3 | 43.2 |
| A29 | 7.4 | 8.1 | 12.3 | 0.4 |
| A31 | 5.4 | 6.2 | 4.4 | 15.3 |
| A32 | 8.8 | 7.1 | 3 | 0.1 |
| A33 | 3.3 | 3.4 | 9 | 13.1 |
| A28* | 77 | 99 | 16.6 | 1.1 |

Abbreviations: EUC, European Caucasian; NAC, North American Caucasian; AFR, African blacks; JPN, Japanese.
*A28 represents the two alleles A268 and A269

The peptides of the invention can be combined via linkage to form polymers (multimers), or can be formulated in a composition without linkage, as an admixture. Where the same peptide is linked to itself, thereby forming a homopolymer, a plurality of repeating epitopic units are presented. When the peptides differ, heteropolymers with repeating units are provided, forming a cocktail of, for example, epitopes specific to different HCV subtypes, different epitopes to the same protein or gene region within a subtype, different epitopes to different proteins or gene regions within a subtype, different HLA restriction specificities, and/or a peptide that contains T helper epitopes. In addition to covalent linkages, noncovalent linkages capable of forming intermolecular and intrastructural bonds are included.

Linkages for homo- or hetero-polymers or for coupling to carriers can be provided in a variety of ways. For example, cysteine residues can be added at both the amino- and carboxy-termini, where the peptides are covalently bonded via controlled oxidation of the cysteine residues. Also useful are a large number of heterobifunctional agents that generate a disulfide link at one functional group end and a peptide link at the other, including N-succidimidyl-3-(2-pyridyl-dithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, *Immun. Rev.*, 62, 185 (1982). Other bifunctional coupling agents form a thioether rather than a disulfide linkage. Many of these thioether forming agents are commercially available (from, for example, Aldrich Chemical Company, Inc., Milwaukee, Wis.) and include reactive esters of 6-maleimidocaproic acid, 2 bromoacetic acid, 2-iodoacetic acid, 4-(N-maleimido-methyl)cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl-4-(n-maleimidomethyl)cyclohexane-1-carboxylate (SMCC). It will be understood that suitable linkage does not substantially interfere with either of the linked groups to function as described, e.g., as a HCV cytotoxic T cell determinant/stimulant, peptide analogs, or T helper determinant/stimulant.

In another aspect of the present invention, the peptides of the invention can be combined or coupled with other suitable peptides that present HCV T-helper cell epitopes, i.e., epitopes that stimulate T cells that cooperate in the induction of cytotoxic T cells to HCV. The T-helper cells can be either the T-helper 1 or T-helper 2 phenotype, for example.

The peptides of the invention can be prepared using any suitable means. Because of their relatively short size (generally, less than 50 amino acids, and preferably less than 20), the peptides can be synthesized in solution or on a solid support in accordance with conventional peptide synthesis techniques. Various automatic synthesizers are commercially available (for example, from Applied Biosystems) and can be used in accordance with known protocols. See, for example, Stewart and Young, *Solid Phase Peptide Synthesis* (2d. ed., Pierce Chemical Co., 1984); Tam et al., *J. Am. Chem. Soc.*, 105, 6442 (1983); Merrifield, *Science*, 232, 341–347 (1986); and Barany and Merrifield, The Peptides (Gross and Meienhofer, eds., Academic Press, New York, 1979), 1–284.

Alternatively, suitable recombinant DNA technology may be employed for the preparation of the peptides of the present invention, wherein a nucleotide sequence that encodes a peptide of interest is inserted into an expression vector, transformed or transfected into a suitable host cell and cultivated under conditions suitable for expression. These procedures are generally known in the art, as described generally in Sambrook et al., *Molecular Cloning, A Laboratory Manual* (2d ed., Cold Spring Harbor Press, Cold Spring Harbor, N.Y., 1989), and *Current Protocols in Molecular Biology* (Ausubel et al., eds., John Wiley and Sons, Inc., New York, 1987), and U.S. Pat. Nos. 4,237,224, 4,273,875, 4,431,739, 4,363,877 and 4,428,941, for example. Thus, recombinant DNA-derived proteins or peptides, which comprise one or more peptide sequences of the invention, can be used to prepare the HCV cytotoxic T cell epitopes identified herein or identified using the methods disclosed herein. For example, a recombinant NS3-derived peptide of the present invention is prepared in which the NS3 amino acid sequence is altered so as to present more effectively epitopes of peptide regions described herein to stimulate a cytotoxic T lymphocyte response. By this means, a polypeptide is used that incorporates several T cell epitopes into a single polypeptide.

As the coding sequence for peptides of the length contemplated herein can be synthesized by chemical techniques, for example, the phosphotriester method of Matteucci et al., *J. Am. Chem. Soc.*, 103, 3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in a suitable cellular host. For example, promoter sequences compatible with bacterial hosts are provided in plasmids containing convenient restriction sites for insertion of the desired coding sequence. The resulting expression vectors are transformed into suitable bacterial hosts. yeast or mammalian cell hosts may also be used, employing suitable vectors and control sequences.

Another aspect of the present invention is directed to a method of provoking an immune response to a hepatitis C viral antigen, comprising contacting a suitable cytotoxic T lymphocyte with an immune response provoking effective amount of a molecule comprising a peptide selected from the group of CTL epitopes recited hereinabove. All of the variations recited hereinabove regarding the molecule of the present invention and the polypeptide that such a molecule includes may be used in the context of the method of provoking an immune response.

Such a contact between the CTL epitope-containing molecule, which may be the CTL epitope alone or a complex of radiolabeled CTL epitope, for example, or some other CTL epitope analog as described above, and a CTL may occur in vitro. Accordingly, after having effected such a contact, after which the CTL's are stimulated with respect to the antigen with which it was placed in contact, the CTL's may then be returned to the originating host for a therapeutic purpose, which is further discussed below. A diagnostic purpose, of course, is satisfied whether the contacted cells are returned to the host or not. That purpose is to answer whether the CTL's of the host can bind the tested epitope and, if so, be stimulated by it, however configured. Indeed, the present invention contemplates various assay methods for detecting in lymphocytes of a mammal cytotoxic T cells that respond to a T cell epitope of hepatitis C virus, which is a consequence of a classic ligand-receptor binding phenomenon. Indeed, the present invention includes assays for the determination of the strength of such binding, using methods well known in the study of ligands and receptors.

A preferred embodiment of the present invention (referred to as Diagnostic 1) is directed to a method of detecting in the lymphocytes of a mammal cytotoxic T cells that respond to a particular T cell epitope of hepatitis C virus, comprising the steps of:

(a) contacting target cells with a molecule comprising at least one of the peptides selected from the group of epitopes recited hereinabove, wherein the target cells are of the same HLA class as the lymphocytes to be tested for the cytotoxic T cells; (b) contacting the lymphocytes to be tested for the cytotoxic T cells with a molecule comprising at least one of the peptides selected from the same group of epitopes listed hereinabove, or ones substantially homologous thereto, under conditions sufficient to restimulate the HCV-specific CTL to respond to appropriate target cells; and (c) determining whether the tested lymphocytes exert a cytotoxic effect on the target cells, thereby indicating the presence of CTL that recognize a T-cell epitope of HCV protein.

Another preferred embodiment (referred to as Diagnostic 2) is directed to a method of detecting in lymphocytes of a mammal CTL's that have receptors that can bind to a particular T cell epitope of HCV, comprising the steps of: (a) contacting the lymphocytes to be tested for the CTL's with a molecule comprising a suitable label and at least one of the peptides selected from the same group of epitopes listed hereinabove, or ones substantially homologous thereto, under suitable conditions of time, temperature, humidity, and salts, nutrients, and pH sufficient to restimulate the HCV-specific CTL to respond to appropriate target cells;

(b) harvesting such contacted cells and washing with medium in the absence of the labeled molecule sufficient to remove any unbound labeled molecule; and (c) measuring the bound labeled molecule using suitable measuring means. Step (b) may alternatively be accomplished by lysing the cells using a hypotonic solution with or without unlabeled molecule or other means known in the art, and preparing a membrane fraction that is free of unbound labeled molecule. A suitable label used in the context of this method includes radioactive isotope tagged molecules, wherein constituent nonradioactive atoms of the molecule have been replaced with radioactive ones, such as $^3H$, $^{14}C$, or $^{35}S$, or if a benzene ring or other suitable group is included in the molecule, $^{125}I$ can be affixed thereto. Other suitable labels include fluorescent groups such as fluorescein isothiocyanate or rhodamine isothiocyanate, that can be affixed covalently to appropriate amino acid side groups using methods well known in the art, as well as enzymes that can convert a substrate from one color to another, such as alkaline phosphatase. A suitable measuring means includes a scintillation gamma ray, or geiger counter and the like, as well as a spectrophotometer, even just a color chart for eyeball comparisons of a reaction color to published standards that indicate certain concentrations of bound ligand, i.e., peptide.

Specific methods used for procuring the cells from a patient, culturing them, and determining the existence and/or extent of cytotoxicity of a given population of cells are well known in the art, one exemplification of which is recited below in Example 2. It is also contemplated that the contacting of host lymphocytes occurring in the aforedescribed diagnostic procedures may take place in vivo on in vitro, and if in vivo, then Diagnostic 1, step (a) and (c) take place in vitro; and Diagnostic 2, (step (b) and (c) also take place in vitro. Accordingly, the present invention provides for the detection of human CTL, for instance in blood or other tissues of patients known or suspected to be infected with HCV, by appropriately adapting methods known for detecting other human CTL. See, for instance, Clerici, et al., *J. Imm.*, 146, 2214–2219 (1991). Additionally, the present invention provides a method to detect cells having receptors specific to the peptides of the present invention.

The assay of this invention is useful for determining whether the immune system of a mammal has been provoked by the above recited epitopes of HCV, thereby to determine whether the occurrence and magnitude of such a response can be correlated with either the occurrence of HCV infection (i.e., for diagnosis) or the severity of the pathogenic effect of the virus (i.e., as a prognostic indicator).

Accordingly, a peptide of the invention may be used to determine the susceptibility of a particular individual to a treatment regimen that employs the peptide or related peptides, and thus may be helpful in modifying an existing treatment protocol or in determining a prognosis for an affected individual. In addition, the peptides may also be used to predict which individuals will be at substantial risk for developing chronic HCV infection.

The contacting between the molecule of the present invention, in any of its various forms, and the CTL that has been described above as an in vitro procedure also preferably occurs in a mammal, including humans and other mammalian species. Introduction of the CTL epitope, in one of its hitherto described forms, may be usefully provided to an individual afflicted with an acute or chronic form of infection, or with no infection at all, in which case the introduction would have a prophylactic effect.

A preferred preparation of the CTL epitope, in whatever form, or, for that matter, of the in vitro stimulated CTL's intended to be reintroduced to a host, is as a pharmaceutical composition. In particular, a pharmaceutical composition of the present invention is comprised of a molecule that includes a polypeptide having substantial homology with a CTL epitope selected from the group of epitopes listed hereinabove, or the polypeptide itself, and a pharmaceutically acceptable carrier.

One skilled in the art will appreciate that suitable methods of administering a compound to a mammal for the treatment of an acute or chronic case of HCV hepatitis, for example, which would be useful in the method of the present invention, are available. Although more than one route can be used to administer a particular compound, a particular route can provide a more immediate and more effective reaction than another route. Accordingly, the described methods provided herein are merely exemplary and are in no way limiting.

Generally, the peptides of the present invention as described above will be administered in a pharmaceutical composition to an individual already infected with HCV. Those in the incubation phase or the acute phase of infection can be treated with the immunogenic peptides separately or in conjunction with other treatments, as appropriate. In therapeutic applications, compositions are administered to a patient in an amount sufficient to elicit an effective cytotoxic T lymphocyte response to HCV and to cure or at least partially arrest its symptoms and/or complications. An amount adequate to accomplish this is defined as a "therapeutically or prophylactically effective dose" which is also an "immune response provoking amount." Amounts effective for a therapeutic or prophylactic use will depend on, e.g., the stage and severity of the disease being treated, the age, weight, and general state of health of the patient, and the judgment of the prescribing physician. The size of the dose will also be determined by the peptide composition, method of administration, timing and frequency of administration as well as the existence, nature, and extent of any adverse side-effects that might accompany the administration of a particular compound or stimulated CTL's and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 µg to about 50 mg of one or more of the compounds described above per kg body weight of the individual. For a 70 kg patient, dosages of from about 10 µg to about 100 mg of peptide would be more commonly used, followed by booster dosages from about 1 µg to about 1 mg of peptide over weeks to months, depending on a patient's CTL response, as determined by measuring HCV-specific CTL activity in PBLs obtained from the patient. For the reintroduction of stimulated CTL's, which were derived from the patient, typically a dose would range upward from 1% of the number of cells removed up to all of them.

It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

Single or multiple administrations of the compositions can be carried out with dose levels and pattern being selected by the treating physician. In any event, the pharmaceutical formulations should provide a quantity of cytotoxic T-lymphocyte stimulatory peptides of the invention sufficient to effectively treat the patient.

For therapeutic use, administration should begin at the first sign of HCV infection or shortly after diagnosis in cases of acute infection, and continue until at least symptoms are substantially abated and for a period thereafter. In well established and chronic cases, loading doses followed by maintenance or booster doses may be required. The elicitation of an effective cytotoxic T lymphocyte response to HCV during treatment of acute hepatitis will minimize the possibility of subsequent development of chronic hepatitis, HCV carrier stage, and ensuing hepatocellular carcinoma.

Treatment of an infected individual with the compositions of the invention may hasten resolution of the infection in acutely infected individuals, the majority of whom are capable of resolving the infection naturally. For those individuals susceptible (or predisposed) to developing chronic infection, the compositions are particularly useful in methods for preventing the evolution from acute to chronic infection. Where the susceptible individuals are identified prior to or during infection, for instance by using the diagnostic procedures described herein, the composition can be targeted to them, minimizing need for administration to a larger population.

The peptide compositions can also be used for the treatment of chronic hepatitis and to stimulate the immune system of carriers to substantially reduce or even eliminate virus-infected cells. Those with chronic hepatitis can be identified as testing positive for virus from about 3–6 months after infection. As individuals may develop chronic HCV infection because of an inadequate (or absent) cytotoxic T lymphocyte response during the acute phase of their infection, it is important to provide an amount of immuno-potentiating peptide in a formulation and mode of administration sufficient to stimulate effectively a cytotoxic T cell response. Thus, for treatment and/or prevention of chronic hepatitis, a representative dose is in the range of about 1 µg to 1,000 mg, preferably about 5 µg to 100 mg for a 70 kg patient per dose. Administration should continue until at least clinical symptoms or laboratory indicators indicate that the HCV infection has been eliminated or substantially abated and for a period thereafter. Immunizing doses followed by maintenance or booster doses at established intervals, e.g., from one to four weeks, may be required, possibly for a prolonged period of time, as necessary to resolve the infection. For the treatment of chronic and carrier HCV infection, it may be desirable to combine the CTL peptides with peptides or proteins that induce immune response to a combination of HCV antigens.

The pharmaceutical compositions for therapeutic treatment are intended for parenteral, topical, oral or local administration and generally comprise a pharmaceutically acceptable carrier and an amount of the active ingredient sufficient to reverse or prevent the bad effects of acute or chronic HCV infection, for example. The carrier may be any of those conventionally used and is limited only by chemico-physical considerations, such as solubility and lack of reactivity with the compound, and by the route of administration.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

The pharmaceutically acceptable excipients described herein, for example, vehicles, adjuvants, carriers or diluents, are well-known to those who are skilled in the art and are readily available to the public. It is preferred that the pharmaceutically acceptable carrier be one that is chemically inert to the active compounds and one that has no detrimental side effects or toxicity under the conditions of use.

The choice of excipient will be determined in part by the particular epitope and epitope formulation chosen, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

Preferably, the pharmaceutical compositions are administered parenterally, e.g., intravenously, subcutaneously, intradermally, or intramuscularly. Thus, the invention provides compositions for parenteral administration that comprise a solution of the cytotoxic T-lymphocyte stimulatory peptides dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J. B. Lippincott Company, Philadelphia, Pa., Banker and Chalmers, eds., pages 238–250, (1982), and *ASHP Handbook on Injectable Drugs*, Toissel, 4th ed., pages 622–630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkylimidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the present invention for application to skin.

Formulations suitable for oral administration require extra considerations considering the peptidyl nature of the epitopes and the likely breakdown thereof if such compounds are administered orally without protecting them from the digestive secretions of the gastrointestinal tract. Such a formulation can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The molecules and/or peptides of the present invention, alone or in combination with other suitable components, can be made into aerosol formulations to be administered via inhalation. For aerosol administration, the cytotoxic T-lymphocyte stimulatory peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25%–5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compounds and polymers useful in the present inventive methods may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In some embodiments, it may be desirable to include in the pharmaceutical composition at least one component that primes CTL generally. Lipids have been identified that are capable of priming CTL in vivo against viral antigens, e.g., tripalmitoyl-S-glycerylcysteinly-seryl-serine ($P_3CSS$), which can effectively prime virus specific cytotoxic T lymphocytes when covalently attached to an appropriate peptide. See, Deres et al., *Nature,* 342, 561–564 (1989). Peptides of the present invention can be coupled to $P_3CSS$, for example and the lipopeptide administered to an individual to specifically prime a cytotoxic T lymphocyte response to HCV. Further, as the induction of neutralizing antibodies can also be primed with $P_3CSS$ conjugated to a peptide that displays an appropriate epitope, e.g., certain NS3 epitopes, the two compositions can be combined to elicit more effectively both humoral and cell-mediated responses to HCV infection.

The concentration of cytotoxic T-lymphocyte stimulatory peptides of the present invention in the pharmaceutical formulations can vary widely, i.e., from less than about 1%, usually at or at least about 10% to as much as 20 to 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of peptide. Actual methods for preparing parenterally administrable compounds will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, the compounds of the present inventive method may be formulated as inclusion complexes, such as cyclodextrin inclusion complexes, or liposomes. Liposomes serve to target the peptides to a particular tissue, such as lymphoid tissue or HCV-infected hepatic cells. Liposomes can also be used to increase the half-life of the peptide composition. Liposomes useful in the present invention include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor, prevalent among lymphoid cells, such as monoclonal antibodies which bind to the CD45 antigen, or with other therapeutic or immunogenic compositions. Thus, liposomes filled with a desired peptide of the invention can be directed to the site of lymphoid or hepatic cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.,* 9, 467 (1980), and U.S. Pat. Nos. 4,235,871, 4,501,728, 4,837,028 and 5,019,369. For targeting to the immune cells, a ligand to be incorporated into the liposome can include, for example, antibodies or fragments thereof specific for cell surface determinants of the desired immune system cells. A liposome suspension containing a peptide may be administered intravenously, locally, topically, etc. in a dose that varies according to the mode of administration, the peptide being delivered, the stage of disease being treated, etc.

In another aspect the present invention is directed to vaccines that contain as an active ingredient an immunogenically effective amount of a cytotoxic T-lymphocyte stimulating peptide, as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of HCV. Useful carriers are well known in the art, and include, e.g., keyhold limpet hemocyanin, thyroglobulin, albumins such as human serum albumin, tetanus toxoid, polyamino acids such as poly(D-lysine:D-glutamic acid), and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum or materials well known in the art. And, as mentioned above, cytotoxic T lymphocyte responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of cytotoxic T-lymphocytes specific for HCV antigen, and the host becomes at least partially immune to HCV infection, or resistant to developing chronic HCV infection.

Vaccine compositions containing the peptides of the invention are administered to a patient susceptible to or otherwise at risk of HCV infection to enhance the patient's own immune response capabilities. Such an amount is defined to be a "immunogenically effective dose" or a "prophylactically effective dose." In this use, the precise amounts again depend on the patient's state of health and weight, the mode of administration, the nature of the formulation, etc., but generally range from about 1.0 µg to about 500 mg per 70 kilogram patient, more commonly from about 50 µg to about 200 mg per 70 kg of body weight. The peptides are administered to individuals of an appropriate HLA type. For example, for vaccine compositions for HLA-A2 individuals, the following peptides can be administered usefully: ADLMGYIPLV (Core$_{131-140}$; SEQ ID NO:1); LLALLSCLTV (Core$_{178-187}$; SEQ ID NO:2); LLCPAGHAV (NS3$_{1169-1177}$; SEQ ID NO:26); KLVALGINAV (NS3$_{1406-1415}$; SEQ ID NO:28); SLMAFTAAV (NS4$_{1789-1797}$; SEQ ID NO:34); LLFNILGGWV (NS4$_{1807-1816}$; SEQ ID NO:35); ILDSFDPLV (NS5$_{2252-2260}$; SEQ ID NO:42); DLMGYIPLV (Core$_{132-140}$; SEQ ID NO:54); and QLRRHIDLLV (E1$_{257-266}$; ID NO:3) and peptides that are substantially homologous thereto.

In some instances, it may be desirable to combine the peptide vaccines of the invention with vaccines directed at neutralizing antibody responses to HCV, particularly to HCV envelope and/or core antigens. Such a vaccine may be composed of, for example, recombinant HCV env- and/or nucleocapside-encoded antigens or purified plasma preparations obtained from HCV-infected individuals. Such vaccines have been developed for hepatitis B virus, which are primarily based on HBsAg and polypeptide fragments thereof.

A combination vaccine directed to prophylaxis or treatment of both HCV and HBV is also contemplated in the present invention. Such a combination vaccine includes antigenic determinants that reflect those of either or both of the B and C hepatitis viruses. For examples of HBV vaccines that can be formulated with the HCV-directed peptides of the present invention, see generally, EP 154,902 and EP 291,586, and U.S. Pat. Nos. 4,565,697, 4,624,918, 4,599,230, 4,599,231, 4,803,164, 4,882,145, 4,977,092, 5,017,558 and 5,019,386. The vaccines can be combined and administered concurrently, or as separate preparations.

For therapeutic or immunization purposes, the peptides of the invention can also be expressed by attenuated viral hosts, such as vaccinia. This approach involves the use of vaccinia virus as a vector to express nucleotide sequences that encode the HCV peptides of the invention. Upon introduction into an acutely or chronically HCV-infected host or into a non-infected host, the recombinant vaccinia virus expresses the HCV peptide and thereby elicits a host cytotoxic T lymphocyte response to HCV. Vaccinia vectors and methods useful in immunization protocols are described in, e.g., U.S. Pat. No. 4,722,848. Another vector is BCG (bacille Calmette Guerin). BCG vectors are described in Stover et al., *Nature*, 351, 456–460 (1991). A wide variety of other vectors useful for therapeutic administration or immunization of the peptides of the invention, e.g., *Salmonella typhi* vectors and the like, will be apparent to those skilled in the art from the description herein.

The compositions and methods of the claimed invention may be employed for ex vivo therapy, wherein, as described briefly above, a portion of a patient's lymphocytes are removed, challenged with a stimulating dose of a peptide of the present invention, and the resultant stimulated CTL's are returned to the patient. Accordingly, in more detail, ex vivo therapy as used herein concerns the therapeutic or immunogenic manipulations that are performed outside the body on lymphocytes or other target cells that have been removed from a patient. Such cells are then cultured in vitro with high doses of the subject peptides, providing a stimulatory concentration of peptide in the cell medium far in excess of levels that could be accomplished or tolerated by the patient. Following treatment to stimulate the CTLs, the cells are returned to the host, thereby treating the HCV infection. The host's cells may also be exposed to vectors that carry genes encoding the peptides, as described above. Once transfected with the vectors, the cells may be propagated in vitro or returned to the patient. The cells that are propagated in vitro may be returned to the patient after reaching a predetermined cell density.

In one method, in vitro CTL responses to HCV are induced by incubating in tissue culture a patient's CTL precursor cells (CTLP) together with a source of antigen-presenting cells (APC) and the appropriate immunogenic peptide. After an appropriate incubation time (typically 1–4 weeks), in which the CTLp are activated and mature and expand into effector CTL, the cells are infused back into the patient, where they will destroy their specific target cell (a HCV infected cell). To optimize the in vitro conditions for the generation of specific cytotoxic T cells, the culture of stimulator cells is typically maintained in an appropriate serum-free medium. Peripheral blood lymphocytes are isolated conveniently following simple venipuncture or leukapheresis of normal donors or patients and used as the responder cell sources of CTLp. In one embodiment, the appropriate APC's are incubated with about 10–100 µM of peptide in serum-free media for four hours under appropriate culture conditions. The peptide-loaded APC are then incubated with the responder cell populations in vitro for 5 to 10 days under optimized culture conditions.

Positive CTL activation can be determined by assaying the cultures for the presence of CTLs that kill radiolabeled target cells, both specific peptide-pulsed targets as well as target cells expressing endogenously processed form of HCV antigen as further discussed below. Specifically, the MHC restriction of the CTL of a patient can be determined by a number of methods known in the art. For instance, CTL restriction can be determined by testing against different peptide target cells expressing appropriate or inappropriate human MHC class I. The peptides that test positive in the MHC binding assays and give rise to specific CTL responses are identified as immunogenic peptides.

The induction of CTL in vitro requires the specific recognition of peptides that are bound to allele specific MHC class I molecules on APC. Peptide loading of empty major histocompatibility complex molecules on cells allows the induction of primary CTL responses. Because mutant cell lines do not exist for every MHC allele, it may be advantageous to use a technique to remove endogenous MHC-associated peptides from the surface of APC, followed by loading the resulting empty MHC molecules with the immunogenic peptides of interest. The use of non-transformed, non-infected cells, and preferably, autologous cells of patients as APC is desirable for the design of CTL induction protocols directed towards development of ex vivo CTL therapies. Typically, prior to incubation of the APCs with the CTLp to be activated, an amount of antigenic peptide is added to the APC or stimulator cell culture, of sufficient quantity to become loaded onto the human Class I molecules to be expressed on the surface of the APCs. Resting or precursor CTLs are then incubated in culture with the appropriate APCs for a time period sufficient to activate the CTLs. Preferably, the CTLs are activated in an antigen-specific manner. The ratio of resting or precursor CTLs to APCs may vary from individual to individual and may further depend upon variables such as the amenability of an individual's lymphocytes to culturing conditions and the nature and severity of the disease condition or other condition for which the described treatment modality is used. Preferably, however, the CTL:APC ratio is in the range of about 30:1 to 300:1. The CTL/APC may be maintained for as long a time as is necessary to stimulate a therapeutically useable or effective number of CTL.

Activated CTL may be effectively separated from the APC using one of a variety of known methods. For example, monoclonal antibodies specific for the APCs, for the peptides loaded onto the stimulator cells, or for the CTL (or a segment thereof) may be utilized to bind their appropriate complementary ligand. Antibody-tagged molecules may then be extracted from the admixture via appropriate means, e.g., via well-known immunoprecipitation or immunoassay methods.

Effective, cytotoxic amounts of the activated CTLs can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD8+ cells are utilized for adult humans, compared to about $5 \times 10^6$ to about $5 \times 10^7$ cells used in mice.

Methods of reintroducing cellular components are known in the art and include procedures such as those exemplified in U.S. Pat. No. 4,844,893 to Honsik, et al. and U.S. Pat. No. 4,690,915 to Rosenberg. For example, administration of activated CTLs via intravenous infusion is typically appropriate.

The following examples further illustrate the present invention but, of course, should not be construed as in any way limiting its scope.

EXAMPLE 1

This example illustrates the identification of peptides that were tested for capability to induce HCV specific responses.

The published HCV-1 amino acid sequence (Choo et al., Proc. Natl. Acad. Sci. USA, 88, 2451–2455 (1991)) was scanned for the presence of the HLA-A2.1 binding motif XLXXXXXXV or XLXXXXXXXV, which sequence is a necessary but not sufficient characteristic for class I restricted CTL stimulation, as described by Falk et al., Nature, 351, 290–296 (1991). From this scan, 53 peptides of 9 or 10 amino acid residues each were identified as putative CTL stimulators. The identified sequences were synthesized by Chiron Mimotopes (Clayton, Australia). The 53 peptides are listed hereinbelow, wherein the single-letter code for amino acids is used: A, Ala; C, Cys; D, Asp; E, Glu; F, Phe; G, Gly; H, His; I, Ile; K, Lys; L, Leu; M, Met; N, Asp; P, Pro; Q, Gln; R, Arg; S, Ser; T, Thr; V, Val; W, Trp; Y, Tyr. The peptides marked with a dagger (†) were found to represent a CTL epitope, using the assay disclosed in Example 2. Information regarding the region of the HCV genome, the amino acid coordinates, and the sequence for each of the 53 selected peptides is included, as follows:

List of HCV-1 Derived Peptides

| HCV-Region | aa Residues | Sequence | Seq. ID No. |
|---|---|---|---|
| Core | 131–140 | ADLMGYIPLV†,* | (SEQ ID NO:1) |
| Core | 178–187 | LLALLSCLTV† | (SEQ ID NO:2) |
| E1 | 257–266 | QLRRHIDLLV | (SEQ ID NO:3) |
| E1 | 279–287 | DLCGSVFLV | (SEQ ID NO:4) |
| E2/NS1 | 402–411 | LLAPGAKQNV | (SEQ ID NO:5) |
| E2/NS1 | 665–674 | LLLTTTQWQV | (SEQ ID NO:6) |
| E2/NS1 | 666–674 | LLTTTQWQV | (SEQ ID NO:7) |
| E2/NS1 | 688–697 | GLIHLHQNIV | (SEQ ID NO:8) |
| E2/NS1 | 691–699 | HLHQNIVDV | (SEQ ID NO:9) |
| E2/NS1 | 723–731 | FLLLADARY | (SEQ ID NO:10) |
| NS2 | 758–766 | SLAGTHGLV | (SEQ ID NO:11) |
| NS2 | 845–853 | WLQYFLTRV | (SEQ ID NO:12) |
| NS2 | 901–909 | ILQASLLKV | (SEQ ID NO:13) |
| NS2 | 905–913 | SLLKVPVFV | (SEQ ID NO:14) |
| NS2 | 906–915 | LILKVPYFVRV | (SEQ ID NO:15) |
| NS2 | 940–949 | KLGALTGTYV | (SEQ ID NO:16) |
| NS2 | 963–971 | GLRDLAVAV | (SEQ ID NO:17) |
| NS2 | 966–974 | DLAVAVEPV | (SEQ ID NO:18) |
| NS2 | 966–975 | DLAVAVEPVV | (SEQ ID NO:19) |
| NS3 | 1069–1077 | FLATCINGV | (SEQ ID NO:20) |
| NS3 | 1010–1019 | ILLGPADGMV | (SEQ ID NO:21) |
| NS3 | 1011–1019 | LLGPADGMV | (SEQ ID NO:22) |
| NS3 | 1046–1055 | SLTGRDKNQV | (SEQ ID NO:23) |
| NS3 | 1131–1139 | YLIVTRHADV | (SEQ ID NO:24) |
| NS3 | 1068–1177 | PLLCPAGHAV | (SEQ ID NO:25) |
| NS3 | 1169–1177 | LLCPAGHAV† | (SEQ ID NO:26) |
| NS3 | 1200–1209 | NLETTMRSPV | (SEQ ID NO:27) |
| NS3 | 1406–1415 | KLVALGINAV† | (SEQ ID NO:28) |
| NS4 | 1529–1537 | ELTPAETTV | (SEQ ID NO:29) |
| NS4 | 1585–1593 | VLVAYQATV | (SEQ ID NO:30) |
| NS4 | 1623–1631 | PLLYRLGAV | (SEQ ID NO:31) |
| NS4 | 1652–1661 | DLEVVTSTWV | (SEQ ID NO:32) |
| NS4 | 1674–1683 | CLSTGCVVIV | (SEQ ID NO:33) |
| NS4 | 1789–1797 | SLMAFTAAV† | (SEQ ID NO:34) |
| NS4 | 1807–1816 | LLFNILGGWV† | (SEQ ID NO:35) |
| NS4 | 1833–1842 | GLAGAAJGSV | (SEQ ID NO:36) |
| NS4 | 1851–1859 | ILAGYGAGV | (SEQ ID NO:37) |
| NS4 | 1886–1894 | ILSPGALVV | (SEQ ID NO:38) |
| NS5 | 2140–2149 | LLREEVSFRV | (SEQ ID NO:39) |
| NS5 | 2159–2168 | QLPCEPEPDV | (SEQ ID NO:40) |
| NS5 | 2189–2198 | RLARGSPPSV | (SEQ ID NO:41) |
| NS5 | 2252–2260 | ILDSFDPLV† | (SEQ ID NO:42) |
| NS5 | 2315–2324 | PLPPKSPPV | (SEQ ID NO:43) |
| NS5 | 2399–2408 | DLSDGSWSTV | (SEQ ID NO:44) |
| NS5 | 2449–2457 | SLLRHHNLV | (SEQ ID NO:45) |
| NS5 | 2479–2487 | VLDSHYQDV | (SEQ ID NO:46) |
| NS5 | 2578–2587 | RLIVFPDLGV | (SEQ ID NO:47) |
| NS5 | 2727–2735 | GLQDCTMLV | (SEQ ID NO:48) |
| NS5 | 2733–2741 | MLVCGDDLV | (SEQ ID NO:49) |
| NS5 | 2733–2742 | MLVCGDDLVV | (SEQ ID NO:50) |
| NS5 | 2781–2790 | ELITSCSSNV | (SEQ ID NO:51) |
| NS5 | 2844–2852 | ILMTHFFSV | (SEQ ID NO:52) |
| NS5 | 2995–3003 | CLLLLAAGV | (SEQ ID NO:53) |
| Core | 132–140 | DLMGYIPLV | (SEQ ID NO:54) |
|  | 257–266 | QLRRHIDLLV | (SEQ ID NO:55) |

In summary, the HCV peptide sequences that satisfy at least one of the HLA-A2.1 binding motifs recited above include two peptides from the core region, two from E1, six from E2/NS1, nine from NS2, nine from NS3, ten from NS4 and 15 from NS5 of the HCV genome. Additionally, the peptide sequence marked with an asterisk (*; SEQ ID NO:1) was found to be more potent in the cytotoxicity assay described below in Example 2 than the same sequence without alanine 131.

EXAMPLE 2

This example sets forth methods used to identify whether a particular polypeptide was able to induce a HCV-specific response in cytotoxic T lymphocytes.

Peripheral blood mononuclear cells ("PBMC") taken from patients afflicted with chronic hepatitis C infection were used to assay CTL-inducing activity of the identified polypeptides. Eight patients were identified who were HLA-A2 positive, as determined by standard micro cytotoxicity tests using HLA typing trays (One Lambda, Canoga Park, Calif.). Each of these patients had chronic hepatitis C infection based on standard clinical parameters and confirmed by liver biopsy, where chronic active hepatitis ("CAH") was in evidence with or without cirrhosis ("C"). Serological assays using the second-generation (c200/c22-3) Ortho HCV ELISA test system (Ortho Diagnostics, Inc., Raritan, N.J.) were conducted as well. The presence of serum HCV RNA was also detected with a "nested" cDNA polymerase chain reaction assay with primers selected from the 5' NC region and subsequent hybridization using an internal probe, as described by Bukh et al., Proc. Natl. Acad. Sci. USA, 89, 187–191 (1992).

Characteristics of Subject Studied

| Subject (Sex) | HLA | ALT | HCV-PCR | Liver Biopsy |
|---|---|---|---|---|
| C-1 (m) | A2, B44, cw3 | 226 | pos. | CAH+C |
| C-2 (f) | A2, A31, B7, B67, Cw7 | 99 | pos. | CAH |
| C-3 (m) | A2, A3, B44, Cw7 | 155 | pos. | CAH |
| C-4 (m) | A2, A30, BW48, BWG4, Cw3 | 79 | pos. | CAH |
| C-5 (f) | A2, A3, B65, B75, Cw1, Cw4 | 97 | pos. | CAH |
| C-6 (f) | A2, A24, B38, B60, Cw3 | 190 | pos. | CAH |
| H-1 (m) | A2, A1, B8, B44, Cw5, Cw7 | nl | pos. | nd■ |
| H-2 (f) | A2, A68, B7801, Cw6 | nl | pos. | nd▲ |

■This subject had no history of hepatitis and had normal liver enzymes; no biopsy was performed.
▲This subject had an episode of acute hepatitis C three months previously; no biopsy was performed.

PBMC from all eight HLA-A2 positive subjects were stimulated individually with the entire panel of 53 peptides, and cultures were tested after initial expansion for peptide specific CTL activity, using the following procedures:

Stimulation of PBMC with synthetic peptides and tetanus toxoid. PBMC from subjects were separated on Ficoll-Hypaque density gradients (Sigma, St. Louis, Mo.), washed three times in Hanks balanced salt solution (HBSS) (Gibco, Grand Island, N.Y.), resuspended in RPMI 1640 medium (Gibco, Grand Island, N.Y.) supplemented with L-glutamine (2 mM), gentamicin (10 µg/ml), penicillin (50 U/ml), streptomycin (50 µg/ml), and HEPES (5 mM) containing 10% heat inactivated human AB serum (complete medium) and plated in 24 well plates at $4\times10^6$ cells/well. The synthetic peptides described in Example 1 were lyophilized and subsequently reconstituted at 20 mg/ml in DMSO (Malinckrodt, Paris, Ky.) and diluted to 1 mg/ml with RPMI 1640 medium (Gibco, Grand Island, N.Y.).

The reconstituted synthetic peptides were then added to the cell cultures at a final concentration of 10 µg/ml. Tetanus toxoid was added at 1 µg/ml during the first week of stimulation. At day 3, 1 ml of complete medium supplemented with rIL-2 (Hoffman-La Roche, Nutley, N.Y.) at 10 U/ml final concentration was added in each well. On day 7, the cultures were restimulated with peptide, rIL-2 and irradiated (3000 rads) autologous feeder cells; the cultured PBMC were tested for CTL activity on day 14. Selected cultures that displayed peptide specific cytolytic activity (see cytotoxicity assay description below) were expanded by weekly restimulation with $1\times10^6$ irradiated (3000 rads) autologous PBMC in 1 ml of complete medium containing 1 µg/ml peptide and 20 U/ml IL-1.

Generation of HCV specific CTL clones. CTL lines were cloned at 0.3, 1, 10, and 100 cells per well and then subcloned at 0.3 or 1 cell per well in 96 well microtiter plates. The cells were plated in the presence of peptide (1 µg/ml), PHA (1 µg/ml), rIL-2 (20 U/ml), irradiated (3000 rads) allogeneic PBMC ($10^5$ cells/well). HCV specific clones were restimulated in a 24 well plate as described above.

Target Cells. Allogeneic and autologous EBV-transformed B lymphoblastoid cell lines (EBV-BCL) were either purchased from The American Society for Histocompatibility and Immunogenetics (Boston, Mass.) or established from our own pool of patients and normal donors. The most commonly used target cell line (JY) is HLA-A2, B7 and Cw7 positive. The cells were maintained in RPMI 1640 supplemented with L-glutamine (2 mM), gentamicin (10 µg/ml), penicillin (50 U/ml), streptomycin (50 µg/ml), HEPES (5 mM), and 10% (vol/vol) heat inactivated fetal calf serum ("FCS"; Gibco, Grand Island, N.Y.). Short term lines of autologous PBMC blasts were produced by stimulating peripheral blood PBMC with PHA at 1 µg/ml in the RPMI 1640 supplemented with L-glutamine (2 mM), gentamicin (10 µg/ml), penicillin (50 U/ml), streptomycin (50 µg/ml). HEPES (5 mM). 10% (vol/vol) heat inactivated FCS, and 10 U/ml rIL-2 for 7 days before use as target cells.

Recombinant expression vectors. Recombinant vaccinia viruses expressing HCV-1 derived sequences were provided by Dr. M. Houghton (Chiron Corporation, Emeryville, Calif.). The constructs used express HCV-1 core/E1 (aa 1–339) and E2/NS2/NS3 (aa 364–1619), respectively.

Generation of recombinant vaccinia viruses was done according to standard procedures as described by Cheng et al., *J. Virol*, 60, 337–344 (1986). Vaccinia infected targets were prepared by infection of $1\times10^6$ cells at 10 to 100 multiplicity of infection ("MOI") on a rocking plate at room temperature for one hour, followed by a single wash and overnight incubation at 37° C.

Cytotoxicity Assay. Target cells consisted of allogeneic HLA matched and mismatched EBV-BCL incubated overnight with synthetic peptides at 10 µg/ml. Target cells were labeled with 100 µCi of $^{51}$Cr (Amersham, Arlington Heights, Ill.) for one hour and washed three times with HBSS. Cytolytic activity was determined in a standard 4 hour $^{51}$Cr-release assay using U-bottom 96 well plates containing 5000 targets per well. All assays were performed in duplicate. Percent cytotoxicity was determined from the formula: 100×[(experimental release—spontaneous release)/(maximum release—spontaneous release)]. Maximum release was determined by lysis of targets by detergent (1% Triton X-100 Sigma). Spontaneous release was less than 25% of maximal release in all assays.

A difference in the specific lysis of peptide pulsed target cells and nonpulsed target cells of 15% at an effector to target cell ratio of 40 to 80/1 in the initial CTL assay performed after 2 weeks of culture was considered to represent a positive CTL response and was confirmed by retesting after additional rounds of restimulation and subsequent cloning.

Flow Cytometry Analysis. Cells to be analyzed ($0.5\times10^6$) were washed once in PBS and then incubated with fluorescent probe-conjugated anti-CD4 and anti-CD8 monoclonal antibody (leu3a. Leu2a) and similarly labeled control antibody (Becton Dickinson & Co.). After a 30-min incubation at 4° C., cells were washed in PBS with 5% BSA and analyzed with a FACScan® flow cytometer (Becton Dickinson & Co.).

EXAMPLE 3

This example illustrates results of studies that demonstrate HCV-specific responses in cytotoxic T lymphocytes by particular polypeptides and that characterize cytotoxic T lymphocyte lines and clones so identified.

CTL response to 7 epitopes in 4 of 8 patients. As described in Example 2, PBMC were stimulated with each of the panel of 53 peptides and the cultures were tested after initial in vitro expansion for peptide specific CTL activity. A difference in the specific lysis of peptide pulsed target cells and nonpulsed target cells of 15% at an effector to target cell ratio of 40/1 to 1/80 was considered to represent a positive CTL response and was confirmed by additional rounds of restimulation and subsequent cloning. FIG. 1 demonstrates the percentage level of activity for each of the positive peptides in a bar graph where the abscissa lists the HCV peptide (identified by a number that is uncoded in the following table) and the ordinate is demarked as percentage specific cytotoxicity.

The result of these assays was that significant cytotoxicity was observed in response to 7 out of 53 peptides tested, as shown in FIG. 1 and summarized in the following table. The peptide specific cytotoxicity after two weeks of culture at an effector to target cell ratio of 40 to 80/1 is shown. Cultures of subject C-3 (Peptide 3) and H-1 (Peptide 5) were tested after three weeks of culture. HLA-A2 matched JY EBV-BCL were used in all cases as target cells.

Summary of HCV-Peptide Specific CTL Responses

| HCV | aa Residues | HCV-Peptide (in FIG. 1) | Subjects Responding |
|---|---|---|---|
| Core | 131–140 | 1 | C-2, C-5 |
| Core | 178–187 | 2 | C-2, C-3 |
| NS3 | 1169–1177 | 3 | C-3 |
| NS3 | 1406–1415 | 4 | C-2, C-3, C-5 |
| NS4 | 1789–1797 | 5 | C-2, H-1 |
| NS4 | 1807–1816 | 6 | C-3 |
| NS5 | 2252–2260 | 7 | C-2 |

In summary, then, four of the eight subjects showed CTL responses to at least one of the 53 peptides. Subject C-2 responded to five peptides, two of which are derived from HCV Core, and one from each of NS3, NS4 and NS5. Subject C-3 responded to four peptides, including HCV $Core_{178-187}$ but not HCV $Core_{131-140}$. C-5 in contrast recognized HCV $Core_{131-140}$ and not HCV $Core_{178-187}$. Subject H-1 responded to only one peptide: $NS4_{1789-1797}$. Several of the peptides were found to be stimulatory for more than one patient, probably reflecting a higher degree of immunogenicity. Four of the subjects (C-1, C-4, C-6, H-2) did not show any significant induction of CTL activity with this panel of peptides or the remaining 46 peptides in the panel employed in this study. CTL responses were detected in 3 of 6 patients with chronic active hepatitis and 1 of 2 subjects with normal liver enzymes.

Figure 2:
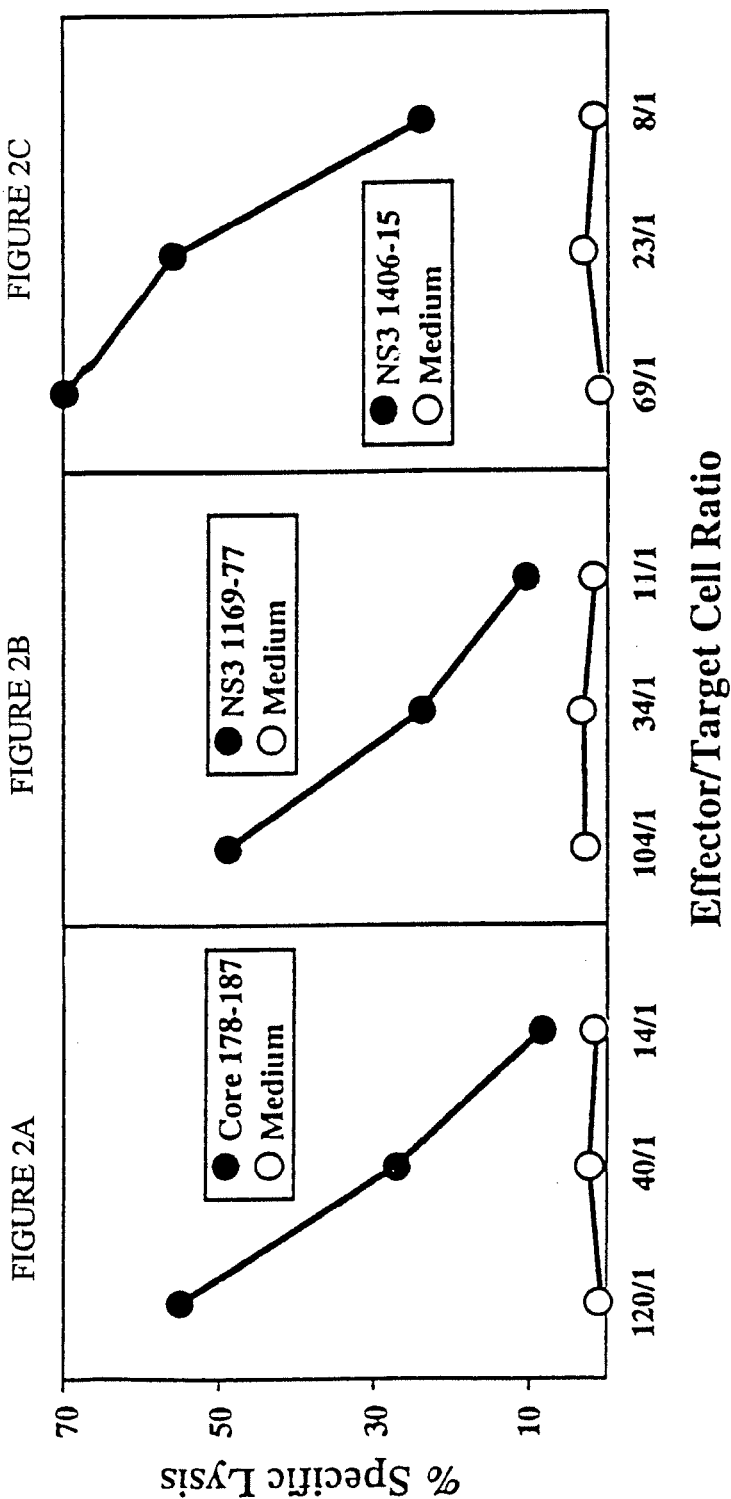

Characterization of HCV peptide specific CTL lines and clones. FIG. 2 displays data derived from an example of typical CTL lines specific for HCV peptides obtained from Subject C-3. The abscissa of FIG. 2 is labeled "Effector/Target Cell Ratio," where "effector" refers to the HCV-peptide used; the ordinate is labeled "% Specific Lysis." Data points indicated by solid circles (●) display specific lysis of peptide-pulsed HLA-A2 matched JY EBV-BCL cells and open circles (○) display specific lysis by unpulsed cultures of the same cells. The CTL lines had been four weeks in culture prior to the CTL assay, and received weekly restimulations with peptides and autologous feeder cells. As shown, these cell lines are specific for HCV $Core_{178-187}$ (panel 2A), $NS3_{1169-1177}$ (panel 2B), and $NS3_{1406-1415}$ (panel 2C) and recognize and lyse HLA A2-matched EBV-BCL in a dose dependent fashion.

In order to establish highly cytotoxic T cell lines for further study and generation of CTL clones, a restimulation protocol involving weekly restimulation with autologous irradiated PBMC, peptide and IL-2 was used. For most of the lines identified, a 2–4 fold increase of cytolytic activity on a per cell basis of each week was observed. For the CTL response of subject C-2 to $NS5_{2252-2260}$, a significant cytotoxic activity after 2 weeks of stimulation of 29% at an E/T ratio of 40/1 was observed. A similar culture using PBMC collected two months later resulted in no significant CTL activity detected after 2 and 3 weeks of stimulation. Continuing restimulation with autologous PBMC and peptide revealed peptide specific CTL after 4 and 5 weeks, however. This may reflect fluctuation of the CTL precursor frequency in the course of HCV infection.

Figure 3:
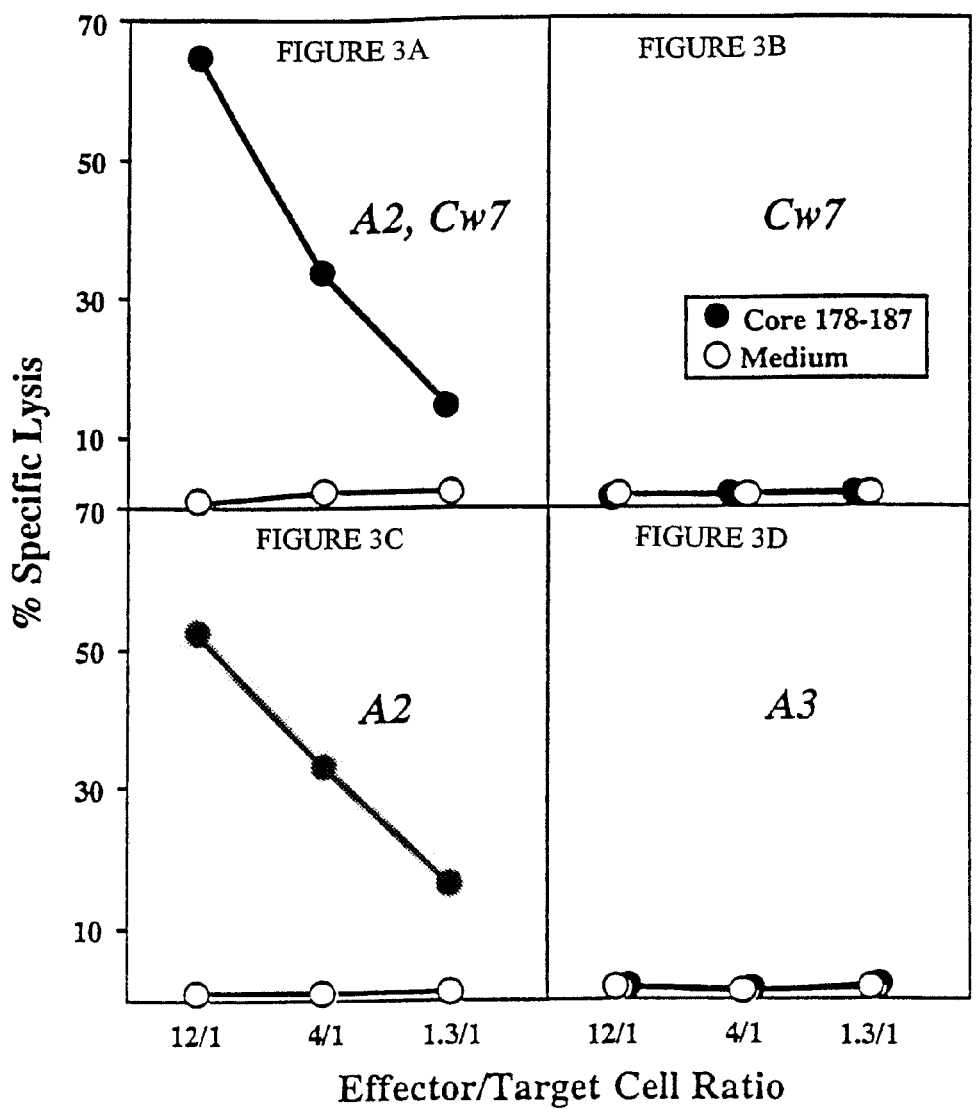

HLA Restriction analysis. An example of an HLA class I restriction analysis is shown in FIG. 3. This analysis is done with a cytotoxicity assay as described in Example 2, using EBV-BCL cells that were peptide pulsed (closed circles; ●) or not peptide pulsed (open circles; ○) and target cells that display different HLA class I alleles, namely HLA-A2/Cw7 (panel 3A), Cw7 (panel 3B), A2 (panel 3C), and A3 (panel 3D). As shown, the presence of the HLA-A2 allele alone is both required and sufficient for recognition and lysis of target cells by the CTL line specific for HCV $core_{178-187}$ derived from subject C-3, who is HLA-A2, A3, B44, Cw7. In view of the CTL induction protocol, rigorous HLA-restriction analysis such as this was not performed because the EBV-BCL target cell most frequently used in our study (JY) is HLA-A2, B7 and Cw7 positive. It is theoretically possible that effectors to $NS4_{1789-1797}$ and $NS5_{2252-2260}$ from subject C-2 recognize epitopes in the context of B7 and Cw7 and those derived from subject H-1 and specific for $NS5_{2252-2260}$ recognize epitopes in the context of Cw7. Effectors from subject C-5 share only the HLA-A2 allele with the target cells.

Cell surface phenotype. Cytotoxic T cell clones were derived from lines by cloning, using limiting dilution as described in Example 2. The resulting six clones were isolated from three donors recognizing epitope $Core_{131-140}$ and $NS3_{1406-1415}$, which clones were used for a test of peptide specific cytotoxic activity at different numbers of effectors per target cell (E/T), which was the JY cell line. The test for cytotoxic activity used was the 4 hour $^{51}$Cr-release assay described in Example 2, the results of which are shown in the table below. The clones from subject C-2 and C-5 were analyzed by flow cytometry and all were found to be CD8$^+$, i.e., all of the clones were restricted to HLA class I.

HCV Specific CTL Clones

| | | | Cytotoxicity | | FACS | |
|---|---|---|---|---|---|---|
| Subject | Peptide | Clone | E/T | % | CD4$^+$ | CD8$^+$ |
| C-2 | $Core_{131-140}$ | R-14-115 | 3 | 67 | 1.4 | 83.6 |
| | | | 1 | 42 | | |
| | | | 0.3 | 27 | | |
| C-5 | $Core_{131-140}$ | H15-17 | 128 | 90 | 2.4 | 84.3 |
| | | | 43 | 97 | | |
| | | | 14 | 94 | | |
| C-5 | $Core_{131-140}$ | H15-26 | 68 | 84 | 1.9 | 97 |
| | | | 22 | 89 | | |
| | | | 7 | 76 | | |
| C-5 | $Core_{131-140}$ | H15-99 | 92 | 90 | 1.7 | 98 |
| | | | 30 | 79 | | |
| | | | 10 | 50 | | |
| C-3 | $NS3_{1406-1415}$ | D55-3 | 0.9 | 44 | nd | nd |
| | | | 0.3 | 16 | | |
| | | | 0.1 | 5 | | |
| C-3 | $NS3_{1406-1415}$ | D55-10 | 18 | 69 | nd | nd |
| | | | 6 | 66 | | |
| | | | 2 | 58 | | |

Figure 4:
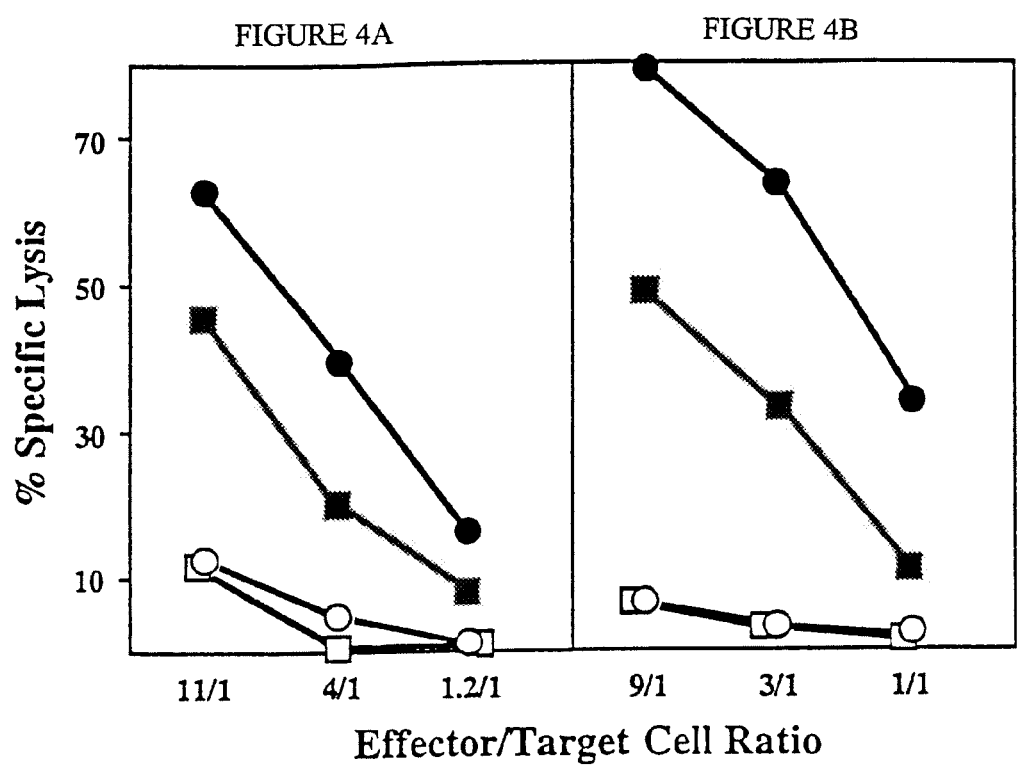

Recognition of endogenous antigen. Recognition and lysis of target cells that synthesize viral antigen endogenously was demonstrated, the results of which are portrayed in FIG. 4. FIG. 4 is divided into two panels, namely panel 4A directed to the analysis of a CTL line from subject C-5 and panel 4B directed to the analysis of the D55-3 clone derived from subject C-3, both of which are specific for $NS3_{1406-1415}$. The abscissa is labeled "Effector/Target Cell Ratio" and the ordinate is labeled "% Specific Lysis." Target cells were HLA-A2 matched EBV-BCL that had been pulsed with $NS3_{1406-1415}$ peptide (closed circles; ●) or medium alone (open circles; ○); or that had been infected with a recombinant vaccinia virus construct containing the HCV amino acid sequence 364–1619 (closed squares; ■) or with the same vaccinia virus without the HCV sequence (open squares; □).

As can be seen in FIG. 4, the CTL line as well as the clone recognize both endogenously synthesized antigen presented by recombinant vaccinia virus infected EBV-BCL as well as exogenously added peptide. Therefore CTL expanded in vitro with peptide retain the ability to recognize and lyse naturally-occurring virus infected target cells.

EXAMPLE 4

This example illustrates a comparison of the sequences of peptides of the present invention to sequences contained in HCV belonging to different isolates.

Using sequences of HCV types deposited in GenEMBL as of January, 1993, a comparative analysis was conducted between the HCV-specific CTL epitopes as represented by the peptides of the present invention and GenEMBL sequences of different isolates of the different HCV subtypes currently identified. See Okamoto et al., *J. Gen. Virol.*, 73, 673–679 (1992). The data is presented below in tabular form, wherein the subtypes are numbered I to IV, ND refers to those HCV isolates where the subtype was not determined, and the results of the comparisons between the listed peptides of the present invention and the corresponding regions of the various HCV subtype genomes is presented as x/y where x is the number of sequences that show no amino acid substitutions within a given epitope and y is the total number of sequences deposited in GenEMBL covering a given epitope.

| HCV | aa Residues | HCV Subtype | | | | |
|---|---|---|---|---|---|---|
| | | I | II | III | IV | ND |
| Core | 131–140 | 3/3 | 8/8 | 1/3 | 2/2 | 7/8 |
| Core | 178–187 | 3/3 | 1/11 | 0/3 | 2/2 | 2/8 |
| NS3 | 1169–1177 | 2/3 | 0/5 | 0/1 | 0/1 | 0/1 |
| NS3 | 1406–1415 | 4/5 | 0/5 | 0/1 | 0/1 | 0/1 |
| NS4 | 1789–1797 | 3/3 | 0/5 | 0/1 | 0/1 | 0/1 |
| NS4 | 1807–1816 | 3/3 | 5/5 | 0/1 | 0/1 | 1/1 |
| NS5 | 2252–2260 | 3/3 | 0/5 | 0/1 | 0/1 | 0/1 |

Accordingly, HCV displays considerable sequence variability, as demonstrated by the above data regarding the known HCV subtypes. It is important for the design of both therapeutic and prophylactic applications of the present invention that peptides be identified that are present in the greatest number of different subtypes predominant in a region of interest. As noted above, the peptide sequence $NS3_{1406-1415}$ (SEQ ID NO:28) was recognized by CTL from three subjects and is present in four out of five HCV I subtypes predominant in the United States and Europe. The fifth isolate, HCV-H, differs only with respect to one conservative Ileu to Val substitution in position 7.

EXAMPLE 5

This example illustrates the ability of a patient's CTL cells to be restimulated by autologous antigen presenting cells.

Using the methods recited in Example 2, PBMC were stimulated with the HCV-derived synthetic peptides of the present invention and restimulated weekly with autologous antigen presenting cells and peptide. Cultures were tested initially after two weeks, then at weekly intervals for peptide specific CTL activity against target cells, as described. In the table below, peptide specific cytotoxic activity is presented for different numbers of effectors per target cell (E/T) obtained in a 4 hour $^{51}Cr$ —release assay for PBMC cells after 2, 3, 4, and 5 weeks of incubation.

For the data concerning subject C-2 and the NS5 peptide, the PBMC for experiment I were collected two months before experiment II. The patient had not received any treatment during this period.

| Subject | Peptide | 2 weeks | | 3 weeks | | 4 weeks | | 5 weeks | |
|---|---|---|---|---|---|---|---|---|---|
| | | E/T | % | E/T | % | E/T | % | E/T | % |
| C-2 | $Core_{131-140}$ | 80 | 61 | 25 | 50 | 72 | 76 | 30 | 76 |
| | | | | | | 24 | 71 | 10 | 78 |
| | | | | | | 8 | 43 | 3 | 51 |
| C-2 | $Core_{178-187}$ | 80 | 29 | 25 | 37 | 64 | 81 | 18 | 60 |
| | | | | | | 21 | 64 | 6 | 57 |
| | | | | | | 7 | 33 | 2 | 24 |
| C-3 | $Core_{178-187}$ | 80 | 19 | 40 | 18 | 33 | 60 | 30 | 76 |
| | | | | | | 11 | 37 | 10 | 52 |
| | | | | | | 4 | 20 | 3 | 35 |
| C-2 | $NS5_{2252-2260}$ Exp I | 40 | 29 | nd | | | | | |
| | $NS5_{2252-2260}$ Exp II | 40 | 2 | 25 | 3 | 88 | 59 | 56 | 83 |
| | | | | | | 29 | 29 | 19 | 52 |
| | | | | | | 10 | 10 | 6 | 20 |
| C-2 | $NS3_{1406-1415}$ | 80 | 24 | 25 | 11 | 56 | 60 | 22 | 29 |
| | | | | | | 19 | 30 | 7 | 14 |
| | | | | | | 6 | 14 | 2 | 7 |

Accordingly, specific cytotoxic activity of circulating cells and their ability to be restimulated were shown, both of which are requisite attributes of a CTL-based vaccine.

EXAMPLE 6

This example illustrates a method for provoking an immune response to molecules containing HCV-derived peptides and/or peptides substantially homologous thereto in a mammal.

Peptide immunization of a mammal with synthetic peptides to induce CD8$^+$ CTL can be performed using 50–100 µg of peptide in complete or incomplete Freund's adjuvant according to the methods of Aichele et al., *J. Exp. Med.*, 171, 1815–1820 (1990) or Kast et al., *Proc. Natl. Acad. Sci USA*, 88, 2283–2287 (1991), or using spleen cells, by the method of Harty et al., *J. Exp. Med.*, 175, 1531–1538 (1992). Protection against HCV infections can be achieved by CTL induced by either of these immunization procedures.

All of the references cited herein, including patents, patent applications, and technical literature, are hereby incorporated in the entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. An isolated molecule comprising a polypeptide that induces an hepatitis C virus (HCV)-specific response in cytotoxic T lymphocytes having a sequence that
   (a) has no more than a total of two single amino acid substitutions, deletions or insertions at the corresponding amino acid positions in a CTL epitope which is
       LLALLSCLTV (Core$_{178-187}$; SEQ ID NO:2),
       QLRRHIDLLV (E1$_{257-266}$; SEQ ID NO:3),
       KLVALGINAV (NS3$_{1406-1415}$; SEQ ID NO:28), or
       LLFNILGGWV (NS4$_{1807-1816}$; SEQ ID NO:35), or
   (b) has no more than one single amino acid substitution, deletion or insertion at the corresponding amino acid positions as in a CTL epitope which is
       ADLMGYIPLV (Core$_{131-140}$; SEQ ID NO:1),
       LLCPAGHAV (NS3$_{1169-1177}$; SEQ ID NO:26), or
       SLMAFTAAV (NS4$_{1789-1797}$; SEQ ID NO:34),
   wherein said molecule comprises at least eight amino acids and less than 50 amino acids, with the provisos that (i) when said selected CTL epitope is SLMAFTAAV (N4$_{1789-1797}$; SEQ ID NO:34), then said molecule comprises from at least eight amino acids to less than 25 amino acids, or (ii) when said selected CTL epitope is LLALLSCLTV (Core$_{178-187}$; SEQ ID NO:2) then said molecule comprises at most ten amino acids.

2. The molecule of claim 1, wherein the isolated peptide has less than 20 amino acids.

3. The molecule of claim 1, wherein the isolated peptide has from 8 to 12 amino acids.

4. The molecule of claim 1, wherein the isolated peptide has 9 or 10 amino acids.

5. The molecule of claim 1, 2, 3, or 4, wherein the isolated molecule has a sequence that has no more than a total of one amino acid substitution, deletion or insertion at the corresponding position as in LLALLSCLTV (Core$_{178-187}$; SEQ ID NO:2).

6. The molecule of claim 1, 2, 3, or 4, wherein the isolated molecule has a sequence that has no more than a total of one amino acid substitution, deletion or insertion at the corresponding position as in QLRRHIDLLV (E1$_{257-266}$; SEQ ID NO:3).

7. The molecule of claim 1, 2, 3, or 4, wherein the isolated molecule has a sequence that has no more than a total of one amino acid substitution, deletion or insertion at the corresponding position as in KLVALGINAV (NS3$_{1406-1415}$; SEQ ID NO:28).

8. The molecule of claim 1, 2, 3, or 4, wherein the isolated molecule has a sequence that has no more than one amino acid substitution, deletion or insertion at the corresponding position as in LLFNILGGWV (NS4$_{1807-1816}$; SEQ ID NO:35).

9. An inunimogenic composition that induces an hepatitis C virus (HCV)-specific response in cytotoxic T lymphocytes (CTL) comprising molecule which comprises a peptide having a sequence that has no more than a total of a total of two amino acid substitutions, deletions or insertions at the corresponding positions as in a CTL epitope which is
    ADLMGYIPLV (Core$_{131-140}$; SEQ ID NO:1),
    LLALLSCLTV (Core$_{178-187}$; SEQ ID NO:2),
    QLRRHIDLLV (E1$_{257-266}$; SEQ ID NO:3),
    KLVALGINAV (NS3$_{1406-1415}$; SEQ ID NO:28), or
    LLFNILGGWV (NS4$_{1807-1816}$; SEQ ID NO:35) or
has no more than a total of one substitution, deletion or insertion at the corresponding amino acid positions as in a CTL epitope which is
    LLCPAGHAV (NS3$_{1169-1177}$; SEQ ID NO:26),
    SLMAFTAAV (NS4$_{1789-1797}$; SEQ ID NO:34), or
    ILDSFDPLV (NS5$_{2252-2260}$; SEQ ID NO:42).

10. The immunogenic composition of claim 9, wherein the immunogenic composition further comprises a label selected from the group consisting of a radioactive label, an enzymatic label, and a fluorescent label.

11. The immunogenic composition of claim 9, wherein the immunogenic composition further comprises a solid matrix.

12. The immunogenic composition of claim 9, wherein the immunogenic composition further comprises a carrier molecule.

13. The immunogenic composition of claim 9, wherein the carrier molecule comprises a protein or an immunogenic lipid.

14. The immunogenic composition of claim 9, wherein the immunogenic composition further comprises a T-helper lymphocyte epitope.

15. The immunogenic composition of claim 9, wherein the immunogenic composition further comprises an additional peptide.

16. The immunogenic composition of claim 15, wherein the additional peptide has a sequence that has no more than a total of two amino acid substitutions, deletions or insertions at the corresponding positions as in KLVALGINAV (NS3$_{1406-1415}$; SEQ ID NO:28).

17. A method of stimulating a cytotoxic T-lymphocyte (CTL) response to an hepatitis C viral immunogen, comprising contacting an HLA class I-restricted cytotoxic T lymphocyte with a composition comprising a peptide that induces an hepatitis C virus (HG V)-specific response in cytotoxic T lymphocytes comprising a sequence that has no more than a total of two single amino acid substitutions, deletions or insertions at the corresponding positions as in a CTL epitope which is ADLMGYIPLV ($Core_{131-140}$; SEQ ID NO:1),
LLALLSCLTV ($Core_{178-187}$; SEQ ID NO:2),
QLRRHIDLLV ($E1_{257-266}$; SEQ ID NO:3),
KLVALGINAV ($NS3_{1406-1415}$; SEQ ID NO:28), or
LLFNILGGWV ($NS4_{1807-1816}$; SEQ ID NO:35) or has no more than a total of one single amino acid substitution, deletion or insertion at the corresponding amino acid positions as in a CTL epitope which is ADLMGYIPLV ($Core_{131-140}$; SEQ ID NO:1),
LLCPAGHAV ($NS3_{1169-1177}$; SEQ ID NO:26),
SLMAFTAAV ($NS4_{1789-1797}$; SEQ ID NO:34), or
ILDSFDPLV ($NS5_{2252-2260}$; SEQ ID NO:42).

18. The method of claim 17, wherein the contacting occurs in a mammal.

19. The method of claim 17, wherein the mammal is free of HCV disease, is a carrier of HCV, or is afflicted with HCV disease.

20. The method of claim 17, wherein the contacting occurs in vitro.

21. The method of claim 17, wherein the peptide comprises the sequence which is ADLMGYIPLV ($Core_{131-140}$; SEQ ID NO:1).

22. A method of detecting cytotoxic T cells that respond to a T cell epitope of hepatitis C virus (HCV), the method comprising the steps of:

(a) preparing HLA class I-restricted cytotoxic T cells;

(b) preparing HLA class-I matched and -mismatched target cells;

(c) containing separately matched and mismatched target cells with a composition comprising a peptide that induces an HCV-specific response in cytotoxic T lymphocytes having the sequence that has no more than a total of two single amino acid substitutions, deletions or insertions at the corresponding positions as in a CTL epitope which is ADLMGYIPLV ($Core_{131-141}$; SEQ ID NO:1),
LLALLSCLTV ($Core_{178-187}$; SEQ ID NO:2),
QLRRHIDLLV ($E1_{257-266}$; SEQ ID NO:3),
KLVALGINAV ($NS3_{1406-1415}$; SEQ ID NO:28), or
LLFNILGGWV ($NS4_{1807-1816}$; SEQ ID NO:35) or has no more than a total of one single amino acid substitution, deletion or insertion at the corresponding amino acid positions as in a CTL epitope which is LLCPAGHAV ($NS3_{1169-1177}$; SEQ ID NO:26),
SLMAFTAAV ($NS4_{1789-1797}$; SEQ ID NO:34), or
ILDSFDPLV ($NS5_{2226-2260}$; SEQ ID NO:42);

(d) combining the cytotoxic T cells separately with the matched and mismatched target cells; and (e) measuring cytolysis.

23. The method of claim 22, wherein the cytotoxic T cells are combined with HLA class I-matched lymphocytes.

24. A pharmaceutical composition comprising a peptide that induces an hepatitis C virus (HCV)-specific response in cytotoxic T lymphocytes having a sequence that has no more than a total of two single amino acid substitutions, deletions or insertions at the corresponding positions as in a CTL epitope which is ADLMGYIPLV ($Core_{131-140}$; SEQ ID NO:1),
LLALLSCLTV ($Core_{178-187}$; SEQ ID NO:2),
QLRRHIDLLV ($E1_{257-266}$; SEQ ID NO:3),
KLVALGINAV ($NS3_{1406-1415}$; SEQ ID NO:28), or
LLFNILGGWV ($NS4_{1807-1816}$; SEQ ID NO:35) or has no more than a total of one single amino acid substitution, deletion or insertion at the corresponding amino acid positions as in a CTL epitope which is LLCPAGHAV ($NS3_{1169-1177}$; SEQ ID NO:26),
SLMAFTAAV ($NS4_{1789-1797}$; SEQ ID NO:34), or
ILDSFDPLV ($NS5_{2252-2226}$; SEQ ID NO:42), and a pharmaceutically acceptable carrier.

25. The pharmaceutical composition of claim 24, wherein the peptide has less than 20 amino acids.

26. A conjugate comprising (a) a molecule, which comprises:

a polypeptide an having no more than a total of two single amino acid substitutions, deletions or insertions at the corresponding positions, as in a CTL epitope which is ADLMGYIPLV ($Core_{131-140}$; SEQ ID NO:1),
LLALLSCLTV ($Core_{178-187}$; SEQ ID NO:2),
QLRRHIDLLV ($E1_{257-266}$; SEQ ID NO:3),
KLVALGINAV ($NS3_{1406-1415}$; SEQ ID NO:28), or
LLFNILGGWV ($NS4_{1807-1816}$; SEQ ID NO:35), or has no more than a total of one single amino acid substitution, deletion or insertion at the corresponding amino acid positions as in a CTL epitope which is LLCPAGHAV ($NS3_{1169-1177}$; SEQ ID NO:26),
SLMAFTAAV ($NS4_{1789-1797}$; SEQ ID NO:34), or
ILDSFDPLV ($NS5_{2252-2260}$; SEQ ID NO:42),; and (b) a substance selected from the group consisting of a radiolabel, an enzyme, a fluorescent label, a solid matrix, a carrier and an additional molecule of (a).

27. The conjugate of claim 26, wherein said carrier comprises an immunogenic lipid or protein.

28. A conjugate of claim 26 comprising two molecules, each comprising:

a polypeptide no more than a total of two single amino acid substitutions, deletions or insertions at the corresponding positions as in a CTL epitope which is ADLMGYIPLV ($Core_{131-140}$; SEQ ID NO:1),
LLALLSCLTV ($Core_{178-187}$; SEQ ID NO:2),
QLRRHIDLLV ($E1_{257-266}$; SEQ ID NO:3),
KLVALGINAV ($NS3_{1406-1415}$; SEQ ID NO:28), or
LLFNILGGWV ($NS4_{1807-1816}$; SEQ ID NO:35), or has no more than a total of one single amino acid substitution, deletion or insertion at the corresponding amino acid positions as in a CTL epitope which is LLCPAGHAV ($NS3_{1169-1177}$; SEQ ID NO:26),
SLMAFTAAV ($NS4_{1789-1797}$; SEQ ID NO:34) or
ILDSFDPLV ($NS5_{2252-2260}$; SEQ ID NO:42).

29. The conjugate of claim 28, wherein at least one of said molecules comprises at least eight amino acids and less than 50 amino acids.

30. The conjugate of claim 28, further comprising a T helper epitope.

31. An isolated molecule comprising a polypeptide that induces an hepatitis C virus (HCV)-specific response in cytotoxic T lymphocytes having a sequence that has (a) no more than a total of two single amino acid substitutions, deletions or insertions at the corresponding amino acid positions in a CTL epitope which is LLALLSCLTV ($Core_{178-187}$; SEQ ID NO:2),
QLRRHIDLLV ($E1_{257-266}$; SEQ ID NO:3),
KLVALGINAV ($NS3_{1406-1415}$; SEQ ID NO:28), or
LLFNILGGWV ($NS4_{1807-1816}$; SEQ ID NO:35), or (b) has no more than one single amino acid substitution, deletion or insertion at the corresponding amino acid positions as in a CTL epitope which is ADLMGYIPLV (Core$_{131-140}$; SEQ ID NO:1),
LLCPAGHAV (NS3$_{1169-1177}$; SEQ ID NO:26), or
SLMAFTAAV (NS4$_{1789-1797}$; SEQ ID NO:34),
wherein said polypeptide comprises at least eight amino acids and less than 50 amino acids, wherein said selected CTL epitope maintains an XaaLeuXaaXaaXaaXaaXaaXaaVal or XaaLeuXaaXaaXaaXaaXaaXaaXaaVal motif,
with the provisos that (a) when said selected CTL epitope is SLMAFTAAV (NS4$_{1789-1797}$; SEQ ID NO:34), then said polypeptide comprises from at least eight amino acids to less than 25 amino acids, and (b) when said selected CTL epitope is LLALLSCLTV (Core$_{178-187}$; SEQ ID NO:2) then said molecule comprises at most ten amino acids.

* * * * *